(12) United States Patent
Alani et al.

(10) Patent No.: US 11,419,822 B2
(45) Date of Patent: Aug. 23, 2022

(54) HIGH CONCENTRATION FORMULATIONS OF ANTI-CSF1 AND ANTI-CSF1R ANTIBODIES

(71) Applicant: AmMax Bio, Inc., Redwood City, CA (US)

(72) Inventors: Laman Alani, Menlo Park, CA (US); Chung-Chiang Hsu, Los Altos Hills, CA (US); Aihua Zhu, Foster City, CA (US); Kirk William Johnson, Moraga, CA (US); Michael Huang, Ladera Ranch, CA (US)

(73) Assignee: AmMax Bio, Inc., Redwood City, CA (US)

( * ) Notice: Subject to any disclaimer, the term of this patent is extended or adjusted under 35 U.S.C. 154(b) by 0 days.

(21) Appl. No.: 17/549,785

(22) Filed: Dec. 13, 2021

(65) Prior Publication Data

US 2022/0183979 A1    Jun. 16, 2022

Related U.S. Application Data

(60) Provisional application No. 63/186,684, filed on May 10, 2021, provisional application No. 63/125,277, filed on Dec. 14, 2020.

(51) Int. Cl.
| | | |
|---|---|---|
| *A61K 39/395* | (2006.01) | |
| *C07K 16/28* | (2006.01) | |
| *A61K 9/19* | (2006.01) | |
| *C07K 16/24* | (2006.01) | |
| *A61K 47/26* | (2006.01) | |
| *A61K 47/18* | (2017.01) | |

(52) U.S. Cl.
CPC .............. *A61K 9/19* (2013.01); *A61K 47/183* (2013.01); *A61K 47/26* (2013.01); *C07K 16/243* (2013.01); *C07K 16/2866* (2013.01)

(58) Field of Classification Search
CPC ..... C07K 16/2866; A61K 9/19; A61K 39/395
See application file for complete search history.

(56) References Cited

U.S. PATENT DOCUMENTS

| | | |
|---|---|---|
| 8,182,813 B2 | 5/2012 | Brasel et al. |
| 2012/0121580 A1 | 5/2012 | Bhambhani et al. |

*Primary Examiner* — Prema M Mertz
(74) *Attorney, Agent, or Firm* — Sheppard Mullin Richter & Hampton LLP

(57) ABSTRACT

Provided are high concentration stable formulations of anti-CSF1R/CSF1 antibodies. An example formulation includes 105 to 250 mg/mL of the antibody, 100 mM to 200 mM of arginine glutamate or arginine HCl, 10 mM to 50 mM histidine, and 0.015 to 0.035 w/v % of polysorbate 80, at a pH of 5.4 to 5.6. Also provided are methods of using the formulations for treating diseases.

13 Claims, 1 Drawing Sheet
Specification includes a Sequence Listing.

SEQUENCE LISTING

<160> NUMBER OF SEQ ID NOS: 16

<210> SEQ ID NO 1
<211> LENGTH: 446
<212> TYPE: PRT
<213> ORGANISM: Artificial Sequence
<220> FEATURE:
<223> OTHER INFORMATION: Synthetic

<400> SEQUENCE: 1

Gln Val Gln Leu Val Gln Ser Gly Ala Glu Val Lys Lys Pro Gly Ala
1               5                   10                  15

-continued

Ser Val Lys Val Ser Cys Lys Ala Ser Gly Tyr Thr Phe Thr Ser Tyr
            20                  25                  30

Asp Ile Ser Trp Val Arg Gln Ala Pro Gly Gln Gly Leu Glu Trp Met
            35                  40                  45

Gly Val Ile Trp Thr Asp Gly Thr Asn Tyr Ala Gln Lys Leu Gln
    50                  55                  60

Gly Arg Val Thr Met Thr Thr Asp Thr Ser Thr Ser Thr Ala Tyr Met
65                  70                  75                  80

Glu Leu Arg Ser Leu Arg Ser Asp Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

```
        Asn His Tyr Thr Gln Lys Ser Leu Ser Leu Ser Pro Gly Lys
                    435                 440                 445

<210> SEQ ID NO 2
<211> LENGTH: 213
<212> TYPE: PRT
<213> ORGANISM: Artificial Sequence
<220> FEATURE:
<223> OTHER INFORMATION: Synthetic

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Ala Ala Ser Asn Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Tyr Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 3
<211> LENGTH: 449
<212> TYPE: PRT
<213> ORGANISM: Artificial Sequence
<220> FEATURE:
<223> OTHER INFORMATION: Synthetic

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
50                  55                  60

Lys Gly Arg Val Thr Ile Thr Ala Asp Lys Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 4
<211> LENGTH: 218
<212> TYPE: PRT
<213> ORGANISM: Artificial Sequence
<220> FEATURE:
<223> OTHER INFORMATION: Synthetic

<400> SEQUENCE: 4

```
Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 5
<211> LENGTH: 450
<212> TYPE: PRT
<213> ORGANISM: Artificial Sequence
<220> FEATURE:
<223> OTHER INFORMATION: Synthetic

<400> SEQUENCE: 5

```
Gln Asp Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Glu Val Asp Tyr Gly Met Asp Val Trp Gly Gln
            100                 105                 110

Gly Thr Thr Val Thr Val Ala Ser Ala Ser Thr Lys Gly Pro Ser Val
        115                 120                 125
```

```
Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 6
<211> LENGTH: 214
<212> TYPE: PRT
<213> ORGANISM: Artificial Sequence
<220> FEATURE:
<223> OTHER INFORMATION: Synthetic

<400> SEQUENCE: 6

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ala
            20                  25                  30
```

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 446
<212> TYPE: PRT
<213> ORGANISM: Artificial Sequence
<220> FEATURE:
<223> OTHER INFORMATION: Synthetic

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ser Trp Phe Gly Glu Val Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

```
Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
        290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 8
<211> LENGTH: 220
<212> TYPE: PRT
<213> ORGANISM: Artificial Sequence
<220> FEATURE:
<223> OTHER INFORMATION: Synthetic

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asp Ser
            20                  25                  30

Ser Asp Asn Lys Asn Tyr Leu Ala Trp Tyr Gln Gln Lys Pro Gly Gln
        35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

Tyr Tyr Ser Asp Pro Phe Thr Phe Gly Pro Gly Thr Lys Val Asp Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 9
<211> LENGTH: 453
<212> TYPE: PRT
<213> ORGANISM: Artificial Sequence
<220> FEATURE:
<223> OTHER INFORMATION: Synthetic

<400> SEQUENCE: 9

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Asp Asp Asp Lys Tyr Tyr Asn Pro Ser
50                  55                  60

Leu Lys Asn Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Gly Pro Ile Lys Tyr Pro Thr Ala Pro Tyr Arg Tyr
            100                 105                 110

Phe Asp Phe Trp Gly Gln Gly Thr Met Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

```
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
    435                 440                 445

Leu Ser Leu Gly Lys
    450

<210> SEQ ID NO 10
<211> LENGTH: 214
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Tyr Asp Asn
            20                  25                  30

Leu Ala Trp Tyr Gln Gln Lys Pro Gly Lys Ala Pro Lys Leu Leu Ile
        35                  40                  45

Tyr Tyr Ala Ser Ser Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Asp Ser Glu Tyr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210
```

<210> SEQ ID NO 11
<211> LENGTH: 448
<212> TYPE: PRT
<213> ORGANISM: Artificial Sequence
<220> FEATURE:
<223> OTHER INFORMATION: Synthetic

<400> SEQUENCE: 11

```
Gln Val Gln Leu Gln Glu Ser Gly Pro Gly Leu Val Lys Pro Ser Gln
1               5                   10                  15

Thr Leu Ser Leu Thr Cys Thr Val Ser Asp Tyr Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Gln Leu Asn Ser Val Thr Ala Ala Asp Thr Ala Val Tyr Tyr Cys
                85                  90                  95

Ala Ser Phe Asp Tyr Ala His Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 12
<211> LENGTH: 214
<212> TYPE: PRT
<213> ORGANISM: Artificial Sequence
<220> FEATURE:
<223> OTHER INFORMATION: Synthetic

<400> SEQUENCE: 12

Asp Ile Val Leu Thr Gln Ser Pro Ala Phe Leu Ser Val Thr Pro Gly
1               5                   10                  15

Glu Lys Val Thr Phe Thr Cys Gln Ala Ser Gln Ser Ile Gly Thr Ser
                20                  25                  30

Ile His Trp Tyr Gln Gln Lys Thr Asp Gln Ala Pro Lys Leu Leu Ile
            35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Ser Ser Val Glu Ala
65                  70                  75                  80

Glu Asp Ala Ala Asp Tyr Tyr Cys Gln Gln Ile Asn Ser Trp Pro Thr
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 13
<211> LENGTH: 447
<212> TYPE: PRT
<213> ORGANISM: Artificial Sequence
<220> FEATURE:
<223> OTHER INFORMATION: Synthetic

<400> SEQUENCE: 13

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ser Phe Asp Tyr Ala His Ala Met Asp Tyr Trp Gly Gln Gly Thr
            100                 105                 110

Ser Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

```
Pro Pro Pro Glu Glu Met Thr Lys Lys Gln Val Thr Leu Thr Cys
            355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly
        435                 440                 445

<210> SEQ ID NO 14
<211> LENGTH: 214
<212> TYPE: PRT
<213> ORGANISM: Artificial Sequence
<220> FEATURE:
<223> OTHER INFORMATION: Synthetic

<400> SEQUENCE: 14

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ile Asn Ser Trp Pro Thr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 15
<211> LENGTH: 447
<212> TYPE: PRT
<213> ORGANISM: Artificial Sequence
<220> FEATURE:
<223> OTHER INFORMATION: Synthetic

<400> SEQUENCE: 15
```

-continued

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Thr Trp Val Arg Gln Ala Pro Gly Lys Gly Leu Glu Trp Val
            35                  40                  45

Ser Tyr Ile Ser Ser Arg Ser Ser Thr Ile Ser Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Pro Leu Leu Ala Gly Ala Thr Phe Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 16
<211> LENGTH: 215
<212> TYPE: PRT
<213> ORGANISM: Artificial Sequence
<220> FEATURE:
<223> OTHER INFORMATION: Synthetic

<400> SEQUENCE: 16

Glu Phe Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

HIGH CONCENTRATION FORMULATIONS OF ANTI-CSF1 AND ANTI-CSF1R ANTIBODIES

CROSS REFERENCE TO RELATED APPLICATIONS

This application claims the benefit under 35 U.S.C. § 119(e) of U.S. Provisional Application Ser. No. 63/125,277 filed Dec. 14, 2020 and 63/186,684, filed May 10, 2021, the content of each of which is incorporated by reference in its entirety into the present disclosure.

BACKGROUND

Colony stimulating factor 1 receptor (CSF1R), also known as macrophage colony-stimulating factor receptor (M-CSFR), and CD115 (Cluster of Differentiation 115), is a cell-surface protein encoded, in humans, by the CSF1R gene (known also as c-FMS). It is a receptor for a cytokine called colony stimulating factor 1 (CSF1).

CSF1R-mediated signaling is crucial for the differentiation and survival of the mononuclear phagocyte system. Intratumoral presence of CSF1R$^+$ macrophages correlates with poor survival in various tumor types, targeting CSF1R signaling in tumor-promoting tumor-associated macrophage represents an attractive strategy to eliminate or repolarize these cells.

A number of anti-CSF1 and anti-CSF1R antibodies are in clinical development, for treating various solid tumors. Examples include emactuzumab (anti-CSF1R, SynOx and Roche), cabiralizumab (anti-CSF1R, Five Prime and BMS), lacnotuzumab (anti-CSF1, Novartis and Xoma), PD-0360324 (anti-CSF1, Pfizer), axatilimab (anti-CSF1R, Syndax and UCB Biopharma), and IMC-CS4 (anti-CSF1R, Eli Lilly and Imclone).

SUMMARY

The present disclosure, in one embodiment, provides formulations (e.g., solutions, suspensions) of anti-CSF1 anti-CSF1R antibodies that allow presence of a relatively high concentration of the antibody, such as at least 80 mg/mL, 100 mg/mL, 150 mg/mL, 180 mg/mL, 200 mg/mL or even 250 mg/mL. Also provided are lyophilized formulations prepared from the aqueous formulation or useful for preparing the aqueous formulation.

Such high concentration formulations allow a small volume of the formulation to be used in a therapy, making subcutaneous injections practical. Unlike intravenous or intramuscular injections which allow injection of a larger volume of a drug product, subcutaneous injections can be done by the patients themselves, without the assistance of a medical professional. The availability of a subcutaneous formulation, therefore, can greatly improve the healthcare of patients, in particular patients having chronic diseases such as tenosynovial giant cell tumor (TGCT), melanoma, glioblastoma, leukemia, and congenital hypertrichosis lanuginosa (CHL). The subcutaneous formulation would provide lower Cmax which would mitigate the potential higher adverse effects associate with high Cmax.

The high concentration formulations also allow other types of administration more effective, such as intraarticular injections, intravenous injections, and intramuscular injections, without limitation. Besides TGCT and other types of tumor, diseases that can also be treated by the instantly disclosed compositions include idiopathic pulmonary fibrosis (IPF), polycystic kidney diseases (PKD), and ocular diseases.

In one embodiment, the present disclosure provides an aqueous pharmaceutical composition comprising at least 105 mg/mL of an antibody, a salt of arginine, histidine, and polysorbate, at a pH of 5.0 to 6.0, preferably 5.4 to 5.8, wherein the antibody is an anti-CSF1R antibody or anti-CSF1 antibody. In some embodiments, the antibody comprises a heavy chain comprising the amino acid sequence of SEQ ID NO:7 and a light chain comprising the amino acid sequence of SEQ ID NO:8.

In some embodiments, the pH is 5.45 to 5.6. In some embodiments, the composition comprises at least 120 mg/mL, preferably at least 140 mg/mL, more preferably at least 150 mg/mL of the antibody. In some embodiments, the salt of arginine is arginine glutamate, arginine aspartate, or arginine HCl. In some embodiments, the salt of arginine is arginine HCl.

In some embodiments, the salt of arginine is present at a concentration of 100 mM to 200 mM, preferably 140 mM to 160 mM, more preferably 145 mM to 155 mM. In some embodiments, the histidine is present at a concentration of 5 mM to 100 mM, preferably 10 mM to 50 mM, more preferably 15 mM to 25 mM. In some embodiments, the polysorbate is polysorbate 80 (PS 80). In some embodiments, the polysorbate is present at a concentration of 0.01 to 0.04 w/v %, preferably 0.015 to 0.035 w/v %, more preferably 0.02 w/v % or 0.03 w/v %.

In some embodiments, the composition does not include lysine, does not include more than 10 mM sucrose or does not include sucrose, does not include more than 5 mM acetate or does not include acetate, does not include more than 10 mM NaCl or does not include NaCl, does not include more than 1 mM citrate or does not include citrate, does not include more than 10 mM of sugar or polyol or does not include sugar or polyol, does not include more than 10 mM succinate, proline or sorbitol or does not include succinate, proline, or sorbitol.

Also provided, in one embodiments, is an aqueous pharmaceutical composition, consisting essentially of 105 to 250 mg/mL of an antibody, 100 mM to 200 mM of arginine glutamate, arginine aspartate, or arginine HCl, 10 mM to 50 mM histidine, and 0.015 to 0.035 w/v % of polysorbate, at a pH of 5.4 to 5.6, wherein the antibody comprises a heavy chain comprising the amino acid sequence of SEQ ID NO:7 and a light chain comprising the amino acid sequence of SEQ ID NO:8. In some embodiments, the composition does not include any of acetate, succinate, citrate, NaCl, sorbitol, lysine, proline, sugar, or polyol.

In another embodiment, the present disclosure provides an aqueous pharmaceutical composition, consisting of 105 to 250 mg/mL of an antibody, 100 mM to 200 mM of arginine glutamate, arginine aspartate, or arginine HCl, 10 mM to 50 mM histidine, and 0.015 to 0.035 w/v % of polysorbate, at a pH of 5.4 to 5.6, wherein the antibody comprises a heavy chain comprising the amino acid sequence of SEQ ID NO:7 and a light chain comprising the amino acid sequence of SEQ ID NO:8. In some embodiments, the composition consists of 140 to 250 mg/mL of the antibody, 120 mM to 180 mM of arginine HCl, 15 mM to 25 mM histidine, and 0.02 to 0.03 w/v % of polysorbate 80, at a pH of 5.45 to 5.55.

Another embodiment provides a method for delivering an anti-CSF1R or anti-CSF1 antibody to a patient, comprising administering to the patient, subcutaneously, the aqueous pharmaceutical composition of the present disclosure. In some embodiments, the patient suffers tenosynovial giant cell tumor (TGCT).

Also provided is a method for treating tenosynovial giant cell tumor (TGCT) in a patient, comprising administering to the patient the aqueous pharmaceutical composition of the present disclosure. In some embodiments, the administration is local to the TGCT. In some embodiments, the local administration is subcutaneous or intraarticular.

Still further provided is a method for treating idiopathic pulmonary fibrosis (IPF) in a patient, comprising administering to the patient the aqueous pharmaceutical composition of the present disclosure. In some embodiments, the administration is systemic.

Also provided are solid compositions that are lyophilized from the aqueous pharmaceutical composition of the present disclosure, or that form the aqueous pharmaceutical composition when added a suitable amount of water.

DETAILED DESCRIPTION

I. Definitions

Figure 1:
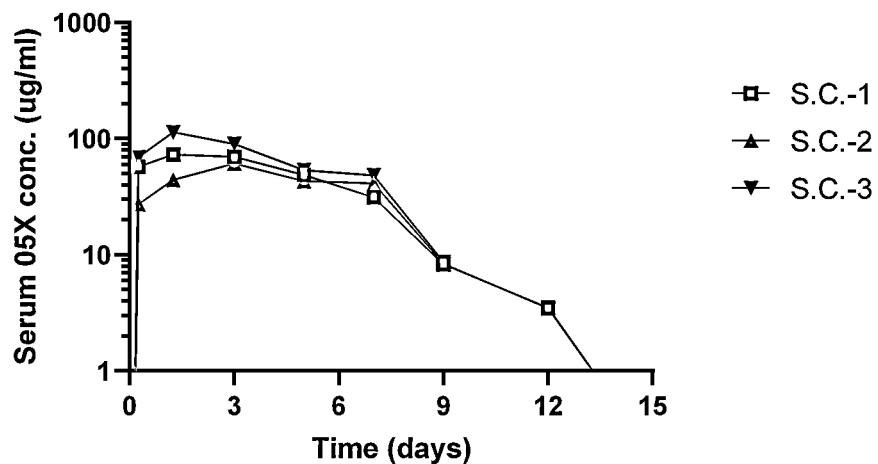
FIG. 1 show serum concentrations of the antibody following administration.

All numerical designations, e.g., pH, temperature, time, concentration, and molecular weight, including ranges, are approximations which are varied (+) or (−) by increments of 0.1 or 10%. It is to be understood, although not always explicitly stated that all numerical designations are preceded by the term "about". It also is to be understood, although not always explicitly stated, that the reagents described herein are merely exemplary and that equivalents of such are known in the art.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

II. Antibody Formulations

Development of a suitable formation for a therapeutic antibody typically has conflicting requirements from, e.g., protein solubility, stability, viscosity, and osmolality. It is therefore challenging and unpredictable whether such requirements could be balanced to generate an acceptable formation.

One embodiment of the present disclosure provides an aqueous formulation of an anti-CSF1 or anti-CSF1R antibody. In some embodiments, the CSF1 or CSF1R antibody is a chimeric monoclonal antibody. In some embodiments, the CSF1 or CSF1R antibody is a human antibody. In some embodiments, the CSF1 or CSF1R antibody is a humanized antibody. In some embodiments, the CSF1 or CSF1R inhibitor is an IgG1 antibody. In some embodiments, the CSF1 or CSF1R antibody is an IgG2a antibody. In some embodiments, the CSF1 or CSF1R antibody is an IgG4 monoclonal. Example anti-CSF1 and anti-CSF1R antibodies are provided in Tables 1A-B below, with representative sequences.

TABLE 1A

Example Anti-CSF1R Antibodies

| Antibody | Protein Sequences |
| --- | --- |
| Emactuzumab (RG7155, or RO5509554) | Heavy chain (SEQ ID NO: 1)<br>QVQLVQSGAEVKKPGASVKVSCKASGYTFTSYDISWVRQAPGQGLEWMGVIWTDGGTNYA<br>QKLQGRVTMTTDTSTSTAYMELRSLRSDDTAVYYCARDQRLYFDVWGQGTTVTVSSASTK<br>GPSVFPLAPSSKSTSGGTAALGCLVKDYFPEPVTVSWNSGALTSGVHTFPAVLQSSGLYS<br>LSSVVTVPSSSLGTQTYICNVNHKPSNTKVDKKVEPKSCDKTHTCPPCPAPELLGGPSVF<br>LFPPKPKDTLMISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKSRWQQGN<br>VFSCSVMHEALHNHYTQKSLSLSPGK<br>Light chain (SEQ ID NO: 2)<br>DIQMTQSPSSLSASVGDRVTITCRASEDVNTYVSWYQQKPGKAPKLLIYAASNRYTGVPS<br>RFSGSGSGTDFTLTISSLQPEDFATYYCQQSFSYPTFGQGTKLEIKRTVAAPSVFIFPPS<br>DEQLKSGTASVVCLLNNFYPREAKVQWKVDNALQSGNSQESVTEQDSKDSTYSLSSTLTL<br>SKADYEKHKVYACEVTHQGLSSPVTKSFNRGEC |
| Cabiralizumab (FPA008) | Heavy chain (SEQ ID NO: 3)<br>QVQLVQSGAEVKKPGSSVKVSCKASGYTFTDNYMIWVRQAPGQGLEWMGDINPYNGGTTF<br>NQKFKGRVTITADKSTSTAYMELSSLRSEDTAVYYCARESPYFSNLYVMDYWGQGTLVTV<br>SSASTKGPSVFPLAPCSRSTSESTAALGCLVKDYFPEPVTVSWNSGALTSGVHTFPAVLQ<br>SSGLYSLSSVVTVPSSSLGTKTYTCNVDHKPSNTKVDKRVESKYGPPCPPCPAPEFLGGP<br>SVFLFPPKPKDTLMISRTPEVTCVVVDVSQEDPEVQFNWYVDGVEVHNAKTKPREEQFNS<br>TYRVVSVLTVLHQDWLNGKEYKCKVSNKGLPSSIEKTISKAKGQPREPQVYTLPPSQEEM<br>TKNQVSLTCLVKGFYPSDIAVEWESNGQPENNYKTTPPVLDSDGSFFLYSRLTVDKSRWQ<br>EGNVFSCSVMHEALHNHYTQKSLSLSLGK<br>Light chain (SEQ ID NO: 4)<br>EIVLTQSPATLSLSPGERATLSCKASQSVDYDGDNYMNWYQQKPGQAPRLLIYAASNLES<br>GIPARFSGSGSGTDFTLTISSLEPEDFAVYYCHLSNEDLSTFGGGTKVEIKRTVAAPSVF<br>IFPPSDEQLKSGTASVVCLLNNFYPREAKVQWKVDNALQSGNSQESVTEQDSKDSTYSLS<br>STLTLSKADYEKHKVYACEVTHQGLSSPVTKSFNRGEC |
| IMC-CS4 (LY3022855) | Heavy chain (SEQ ID NO: 5)<br>QDQLVESGGGVVQPGRSLRLSCAASGFTFSSYGMHWVRQAPGEGLEWVAVIWYDGSNKYY<br>ADSVKGRFTISRDNSKNTLYLQMNSLRAEDTAVYYCARGDYEVDYGMDVWGQGTTVTVAS |

TABLE 1A-continued

Example Anti-CSF1R Antibodies

| Antibody | Protein Sequences |
|---|---|
| | ASTKGPSVFPLAPSSKSTSGGTAALGCLVKDYFPEPVTVSWNSGALTSGVHTFPAVLQSS<br>GLYSLSSVVTVPSSSLGTQTYICNVNHKPSNTKVDKRVEPKSCDKTHTCPPCPAPELLGG<br>PSVFLFPPKPKDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLTVDKSRW<br>QQGNVFSCSVMHEALHNHYTQKSLSLSPGK<br>Light chain (SEQ ID NO: 6)<br>AIQLTQSPSSLSASVGDRVTITCRASQGISNALAWYQQKPGKAPKLLIYDASSLESGVPS<br>RFSGSGSGTDFTLTISSLQPEDFATYYCQQFNSYPWTFGQGTKVEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |
| AM001 | Heavy chain (SEQ ID NO: 7)<br>QVQLVQSGAEVKKPGASVKVSCKASGYTFTSYGISWVRQAPGQGLEWMGWISAYNGNTNY<br>AQKLQGRVTMTTDTSTSTAYMELRSLRSDDTAVYYCARESWFGEVFFDYWGQGTLVTVSS<br>ASTKGPSVFPLAPCSRSTSESTAALGCLVKDYFPEPVTVSWNSGALTSGVHTFPAVLQSS<br>GLYSLSSVVTVPSSNFGTQTYTCNVDHKPSNTKVDKTVERKCCVECPPCPAPPVAGPSVF<br>LFPPKPKDTLMISRTPEVTCVVVDVSHEDPEVQFNWYVDGVEVHNAKTKPREEQFNSTFR<br>VVSVLTVVHQDWLNGKEYKCKVSNKGLPAPIEKTISKTKGQPREPQVYTLPPSREEMTKN<br>QVSLTCLVKGFYPSDIAVEWESNGQPENNYKTTPPMLDSDGSFFLYSKLTVDKSRWQQGN<br>VFSCSVMHEALHNHYTQKSLSLSPGK<br>Light chain (SEQ ID NO: 8)<br>DIVMTQSPDSLAVSLGERATINCKSSQSVLDSSDNKNYLAWYQQKPGQPPKLLIYWASNR<br>ESGVPDRFSGSGSGTDFTLTISSLQAEDVAVYYCQQYYSDPFTFGPGTKVDIKRTVAAPS<br>VFIFPPSDEQLKSGTASVVCLLNNFYPREAKVQWKVDNALQSGNSQESVTEQDSKDSTYS<br>LSSTLTLSKADYEKHKVYACEVTHQGLSSPVTKSFNRGEC |
| Axatilimab (SNDX-6352) | Heavy chain (SEQ ID NO: 9)<br>EVTLKESGPALVKPTQTLTLTCTFSGFSLTTYGMGVGWIRQPPGKALEWLANIWWDDDKY<br>YNPSLKNRLTISKDTSKNQVVLTMTNMDPVDTATYYCARIGPIKYPTAPYRYFDFWGQGT<br>MVTVSSASTKGPSVFPLAPCSRSTSESTAALGCLVKDYFPEPVTVSWNSGALTSGVHTFP<br>AVLQSSGLYSLSSVVTVPSSSLGTKTYTCNVDHKPSNTKVDKRVESKYGPPCPPCPAPEF<br>LGGPSVFLFPPKPKDTLMISRTPEVTCVVVDVSQEDPEVQFNWYVDGVEVHNAKTKPREE<br>QFNSTYRVVSVLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYSRLTVDK<br>SRWQEGNVFSCSVMHEALHNHYTQKSLSLSLGK<br>Light chain (SEQ ID NO: 10)<br>DIQMTQSPSSLSASVGDRVTITCLASEDIYDNLAWYQQKPGKAPKLLIYYASSLQDGVPS<br>RFSGSGSGTDYTLTISSLQPEDFATYYCLQDSEYPWTFGGGTKVEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |

TABLE 1B

Example Anti-CSF1 Antibodies

| Antibody | Protein Sequences |
|---|---|
| Lacnotuzumab (MCS110) | Heavy chain (SEQ ID NO: 11)<br>QVQLQESGPGLVKPSQTLSLTCTVSDYSITSDYAWNWIRQFPGKGLEWMGYISYSGSTSY<br>NPSLKSRITISRDTSKNQFSLQLNSVTAADTAVYYCASFDYAHAMDYWGQGTTVTVSSAS<br>TKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKRVEPKSCDKTHTCPPCPAPELLGGPS<br>VFLFPPKPKDTLMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQVYTLPPSREEMT<br>KNQVSLTCLVKGFYPSDIAVEWESNGQPENNYKTTPPVLDSDGSFFLYSKLTVDKSRWQQ<br>GNVFSCSVMHEALHNHYTQKSLSLSPGK<br>Light chain (SEQ ID NO: 12)<br>DIVLTQSPAFLSVTPGEKVTFTCQASQSIGTSIHWYQQKTDQAPKLLIKYASESISGIPS<br>RFSGSGSGTDFTLTISSVEAEDAADYYCQQINSWPTTFGGGTKLEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |
| MCS110 var | Heavy chain (SEQ ID NO: 13)<br>DVQLQESGPGLVKPSQSLSLTCTVTDYSITSDYAWNWIRQFPGNKLEWMGYISYSGSTSY<br>NPSLKSRISITRDTSKNQFFLQLNSVTTEDTATYYCASFDYAHAMDYWGQGTSVTVSSAK<br>TTAPSVYPLAPVCGDTTGSSVTLGCLVKGYFPEPVTLTWNSGSLSSGVHTFPAVLQSDLY<br>TLSSSVTVTSSTWPSQSITCNVAHPASSTKVDKKIEPRGPTIKPCPPCKCPAPNLLGGPS<br>VFIFPPKIKDVLMISLSPIVTCVVVDVSEDDPDVQISWFVNNVEVHTAQTQTHREDYNST<br>LRVVSALPIQHQDWMSGKEFKCKVNNKDLPAPIERTISKPKGSVRAPQVYVLPPPEEEMT<br>KKQVTLTCMVTDFMPEDIYVEWTNNGKTELNYKNTEPVLDSDGSYFMYSKLRVEKKNWVE<br>RNSYSCSVHEGLHNHHTTKSFSRTPG<br>Light chain (SEQ ID NO: 14) |

TABLE 1B-continued

Example Anti-CSF1 Antibodies

| Antibody | Protein Sequences |
|---|---|
| | DILLTQSPAILSVSPGERVSFSCRASQSIGTSIHWYQQRTNGSPRLLIKYASESISGIPS<br>RFSGSGSGTDFTLSINSVESEDIADYYCQQINSWPTTFGGGTKLEIKRADAAPTVSIFPP<br>SSEQLTSGGASVVCFLNNFYPKDINVKWKIDGSERQNGVLNSWTDQDSKDSTYSMSSTLT<br>LTKDEYERHNSYTCEATHKTSTSPIVKSFNRNEC |
| PD-0360324 | Heavy chain (SEQ ID NO: 15)<br>EVQLVESGGGLVQPGGSLRLSCAASGFTFSSFSMTWVRQAPGKGLEWVSYISSRSSTISY<br>ADSVKGRFTISRDNAKNSLYLQMNSLRDEDTAVYYCARDPLLAGATFFDYWGQGTLVTVS<br>SASTKGPSVFPLAPCSRSTSESTAALGCLVKDYFPEPVTVSWNSGALTSGVHTFPAVLQS<br>SGLYSLSSVVTVPSSNFGTQTYTCNVDHKPSNTKVDKTVERKCCVECPPCPAPPVAGPSV<br>FLFPPKPKDTLMISRTPEVTCVVVDVSHEDPEVQFNWYVDGVEVHNAKTKPREEQFNSTF<br>RVVSVLTVVHQDWLNGKEYKCKVSNKGLPAPIEKTISKTKGQPREPQVYTLPPSREEMTK<br>NQVSLTCLVKGFYPSDIAVEWESNGQPENNYKTTPPMLDSDGSFFLYSKLTVDKSRWQQG<br>NVFSCSVMHEALHNHYTQKSLSLSPGK<br>Light chain (SEQ ID NO: 16)<br>EFVLTQSPGTLSLSPGERATLSCRASQSVSSSYLAWYQQKPGQAPRLLIYGASSRATGIP<br>DRFSGSGSGTDFTLTISRLEPEDFAVYYCQQYGSSPLTFGGGTKVEIKRTVAAPSVFIFP<br>PSDEQLKSGTASVVCLLNNFYPREAKVQWKVDNALQSGNSQESVTEQDSKDSTYSLSSTL<br>TLSKADYEKHKVYACEVTHQGLSSPVTKSFNRGEC |

Emactuzumab (also known as RG7155 and RO5509554) is a clinical stage humanized IgG1 CSF1R targeted antibody designed to target and deplete macrophages in the tumor tissue. It has shown a favorable safety profile in patients and encouraging efficacy for TGCT. Emactuzumab is under investigation in clinical trial NCT01494688—"A Study of RO5509554 as Monotherapy and in Combination with Paclitaxel in Participants With Advanced Solid Tumors."

Cabiralizumab (also known as FPA008) is under investigation in clinical trial NCT03502330—"APX005M With Nivolumab and Cabiralizumab in Advanced Melanoma, Non-small Cell Lung Cancer or Renal Cell Carcinoma." Cabiralizumab is a humanized IgG4 anti-CSF1R monoclonal antibody with a single amino acid substitution in the hinge region to prevent hemi-dimer exchange.

IMC-CS4 (also known as LY3022855) is a human IgG1 antibody (mAb) targeting CSF1R. IMC-CS4 is under investigation in clinical trial NCT01346358—"A Study of IMC-CS4 in Subjects With Advanced Solid Tumors."

AM001 is a fully human IgG2 anti-CSF1R antibody. Other example anti-CSF1R antibodies include PD-0360324 and GTX128677, without limitation.

Axatilimab (also known as SNDX-6352) is a humanized, full-length IgG4 antibody with high affinity to CSF-1R. Axatilimab affects the migration, proliferation, differentiation, and survival of monocytes and macrophages by binding to CSF-1R and blocking its activation by its two known ligands, CSF-1 and IL-34. Axatilimab is currently being evaluated in a Phase 1/2 clinical trial in patients with cGVHD.

Lacnotuzumab (also known as MCS110) is a high-affinity human engineered anti-CSF1 antibody that blocks the ability of CSF1R to drive proliferation in responsive cells. Lacnotuzumab is under investigation in clinical trial NCT01643850—"MCS110 in Patients With Pigmented Villonodular Synovitis (PVNS)."

PD-0360324 is a fully human immunoglobulin G2 monoclonal antibody against CSF1 investigated for treating cutaneous lupus erythematosus (CLE). It is also being tested for its combination with Cyclophosphamide in treating patients with recurrent high-grade epithelial ovarian, primary peritoneal, or fallopian tube cancer.

The present disclosure, in one embodiment, provides aqueous formulations of an anti-CSF1 or anti-CSF1R antibody at a concentration that is at least about 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, or even 250 mg/mL. In some embodiments, the concentration is not higher than about 500 mg/mL, 400 mg/mL, or 300 mg/mL.

High concentration antibody formulations are challenging to develop. For instance, it is known that high concentrations (≥150 mg/mL) of proteins in a solution can lead to dramatically increased solution viscosities, which in turn can lead to stability, manufacturing and delivery challenges. Protein-protein interactions (PPI) can occur in such solutions, which can result in concentration dependent elevated viscosities in highly concentrated antibody solutions arising from a crowded environment of antibodies forming reversible PPI leading to undesirable behavior. Additionally, PPI can contribute to issues such as protein aggregation, undesirable levels of solution opalescence, and in some cases, liquid-liquid phase separation. This association of mAb molecules has been attributed to several transient interactions such as electrostatic, hydrophobic, dipole-dipole, hydrogen bonding, and van der Waals interactions. Yet another challenge, in particular for subcutaneous injection, is to maintain isotonicity.

The accompanying experimental examples took AM001 as an example antibody. Not surprisingly, many commonly used formulation excipients and conditions (e.g., pH ranges) were determined to be unsuitable for formulating this antibody at high concentrations (e.g., at about 150 mg/mL), with acceptable physical and chemical stability and low viscosity. For instance, inclusion of NaCl at even 50 mM caused obvious opalescence of and also destabilized the samples. In addition, common excipients such as citrate, sugars, polyols, succinate, proline, and sorbitol also resulted in decreased stability or increased viscosity. Also surprisingly, even though lysine is structurally and functionally similar to arginine, inclusion of lysine in the formulation as an excipient led to increased turbidity.

Typically, for an antibody, the suitable stabilizing pH range is 6.0 to 7.0. Surprisingly, for AM001, at a pH above 6, acidic peaks started to be detected presumably due to deamidation. Low pH such as <5 were also shown to destabilize the antibody.

Fortunately, after many trials and errors, the instant inventors were able find a small number of excipients and a fairly narrow and low pH range that not only kept the antibody stable with low viscosity, also allowed the antibody to be included at a high concentration, suitable for subcutaneous injections and other routes of administration.

In accordance with one embodiment of the present disclosure, provided is an aqueous pharmaceutical composition that includes at least 105 mg/mL of an antibody, a salt of arginine, histidine, and polysorbate, at a pH of 5.4 to 5.8, wherein the antibody is an anti-CSF1R antibody or anti-CSF1 antibody. Example antibodies are provided in Table 1A-B. In a preferred embodiment, the antibody is AM001. As shown in the tables, AM001 includes a heavy chain of the amino acid sequence of SEQ ID NO:7 and a light chain of the amino acid sequence of SEQ ID NO:8.

In some embodiments, the composition comprises at least 105 mg/mL of the antibody. In some embodiments, the antibody concentration is at least 110 mg/mL, 115 mg/mL, 120 mg/mL, 125 mg/mL, 130 mg/mL, 135 mg/mL, 140 mg/mL, 145 mg/mL, 150 mg/mL, 155 mg/mL, 160 mg/mL, 165 mg/mL, 170 mg/mL, 175 mg/mL, 180 mg/mL, 185 mg/mL, 190 mg/mL, 195 mg/mL or 200 mg/mL. In some embodiments, the antibody concentration is 105 mg/mL to 300 mg/mL, 120 mg/mL to 250 mg/mL, 120 mg/mL to 200 mg/mL, 130 mg/mL to 180 mg/mL, 140 mg/mL to 170 mg/mL, without limitation.

In some embodiments, the pH is 5.0 to 6.0, 5.1 to 5.9, 5.2 to 5.9, 5.3 to 5.9, 5.4 to 5.8, or 5.4 to 5.7, 5.45 to 5.65, 5.45 to 5.6, 5.45 to 5.55, 5.48 to 5.52, 5.49 to 5.51, or at 5.5.

In some embodiments, the salt of arginine is arginine glutamate, arginine aspartate, or arginine HCl, without limitation. In some embodiments, the salt of arginine is preferably arginine HCl. In some embodiments, the salt of arginine is present at a concentration of 100 mM to 200 mM, preferably 120 mM to 180 mM, 140 mM to 160 mM, or more preferably 145 mM to 155 mM. In some embodiments, the arginine HCl is present at a concentration of 100 mM to 200 mM, preferably 120 mM to 180 mM, 140 mM to 160 mM, or more preferably 145 mM to 155 mM, or at about 150 mM.

In some embodiments, the histidine is present at a concentration of 5 mM to 100 mM, preferably 10 mM to 50 mM, more preferably 15 mM to 25 mM, 18 mM to 22 mM, or at about 20 mM.

In some embodiments, the polysorbate is polysorbate 80 (PS 80). In some embodiments, the PS 80 is present at a concentration of 0.01 to 0.04 w/v %, preferably 0.015 to 0.035 w/v %, 0.015 to 0.025 w/v % or 0.025 to 0.035 w/v %, more preferably 0.02 w/v % or 0.03 w/v %.

In an example embodiment, the aqueous pharmaceutical composition consisting essentially of 105 to 250 mg/mL of AM001, 100 mM to 200 mM of arginine glutamate, arginine aspartate, or arginine HCl, 10 mM to 50 mM histidine, and 0.015 to 0.035 w/v % of polysorbate, at a pH of 5.4 to 5.6. In anther example embodiments, the aqueous pharmaceutical composition consisting of (including the following but excluding any other ingredient not explicitly recited) 105 to 250 mg/mL of AM001, 100 mM to 200 mM of arginine glutamate, arginine aspartate, or arginine HCl, 10 mM to 50 mM histidine, and 0.015 to 0.035 w/v % of polysorbate 80, at a pH of 5.4 to 5.6.

In some embodiments, the composition consists of 140 to 250 mg/mL of AM001, 120 mM to 180 mM of arginine HCl, 15 mM to 25 mM histidine, and 0.02 to 0.03 w/v % of polysorbate, at a pH of 5.45 to 5.55. In some embodiments, the composition consists of 140 to 200 mg/mL of AM001, 140 mM to 160 mM of arginine HCl, 15 mM to 25 mM histidine, and 0.02 to 0.03 w/v % of polysorbate 80, at a pH of 5.45 to 5.55.

In some embodiments, the composition does not include excipients that have been tested to be detrimental to the stability, viscosity, or solubility of the formulation. In some embodiments, the excipient to be limited or excluded is lysine. Accordingly, in some embodiments, the composition does not include more than 50 mM, 40 mM, 30 mM, 20 mM, 10 mM, 5 mM, 2 mM, 1 mM, 0.5 mM, or 0.1 mM lysine. In some embodiments, the composition does not include any lysine.

In some embodiments, the excipient to be limited or excluded is sucrose. Accordingly, in some embodiments, the composition does not include more than 50 mM, 40 mM, 30 mM, 20 mM, 10 mM, 5 mM, 2 mM, 1 mM, 0.5 mM, or 0.1 mM sucrose. In some embodiments, the composition does not include any sucrose.

In some embodiments, the excipient to be limited or excluded is acetate. Accordingly, in some embodiments, the composition does not include more than 50 mM, 40 mM, 30 mM, 20 mM, 10 mM, 5 mM, 2 mM, 1 mM, 0.5 mM, or 0.1 mM acetate. In some embodiments, the composition does not include any acetate.

In some embodiments, the excipient to be limited or excluded is acetate. Accordingly, in some embodiments, the composition does not include more than 50 mM, 40 mM, 30 mM, 20 mM, 10 mM, 5 mM, 2 mM, 1 mM, 0.5 mM, or 0.1 mM acetate. In some embodiments, the composition does not include any acetate.

In some embodiments, the excipient to be limited or excluded is NaCl (or any other metal ions, such as $K^+$, $Ca^{2+}$). Accordingly, in some embodiments, the composition does not include more than 50 mM, 40 mM, 30 mM, 20 mM, 10 mM, 5 mM, 2 mM, 1 mM, 0.5 mM, or 0.1 mM NaCl (or any other metal ions, such as $K^+$, $Ca^{2+}$). In some embodiments, the composition does not include any NaCl (or any other metal ions, such as $K^+$, $Ca^{2+}$).

In some embodiments, the excipient to be limited or excluded is citrate. Accordingly, in some embodiments, the composition does not include more than 50 mM, 40 mM, 30 mM, 20 mM, 10 mM, 5 mM, 2 mM, 1 mM, 0.5 mM, 0.1 mM, 0.05 mM, 0.01 mM, 0.005 mM, or 0.001 mM citrate. In some embodiments, the composition does not include any citrate.

In some embodiments, the excipient to be limited or excluded is sugar or polyol. Accordingly, in some embodiments, the composition does not include more than 50 mM, 40 mM, 30 mM, 20 mM, 10 mM, 5 mM, 2 mM, 1 mM, 0.5 mM, 0.1 mM, 0.05 mM, 0.01 mM, 0.005 mM, or 0.001 mM sugar or polyol. In some embodiments, the composition does not include any sugar or polyol.

In some embodiments, the excipient to be limited or excluded is succinate. Accordingly, in some embodiments, the composition does not include more than 50 mM, 40 mM, 30 mM, 20 mM, 10 mM, 5 mM, 2 mM, 1 mM, 0.5 mM, 0.1 mM, 0.05 mM, 0.01 mM, 0.005 mM, or 0.001 mM succinate. In some embodiments, the composition does not include any succinate.

In some embodiments, the excipient to be limited or excluded is sorbitol. Accordingly, in some embodiments, the composition does not include more than 50 mM, 40 mM, 30 mM, 20 mM, 10 mM, 5 mM, 2 mM, 1 mM, 0.5 mM, 0.1 mM, 0.05 mM, 0.01 mM, 0.005 mM, or 0.001 mM sorbitol. In some embodiments, the composition does not include any sorbitol.

In some embodiments, the excipient to be limited or excluded is proline. Accordingly, in some embodiments, the composition does not include more than 50 mM, 40 mM, 30 mM, 20 mM, 10 mM, 5 mM, 2 mM, 1 mM, 0.5 mM, 0.1 mM, 0.05 mM, 0.01 mM, 0.005 mM, or 0.001 mM proline. In some embodiments, the composition does not include any proline.

In some embodiments, the excipient to be limited or excluded is any amino acid other than arginine or histidine (or glutamate/aspartate if included). Accordingly, in some embodiments, the composition does not include more than 50 mM, 40 mM, 30 mM, 20 mM, 10 mM, 5 mM, 2 mM, 1 mM, 0.5 mM, 0.1 mM, 0.05 mM, 0.01 mM, 0.005 mM, or 0.001 mM of any amino acid other than arginine or histidine (or glutamate/aspartate if included). In some embodiments, the composition does not include any amino acid other than arginine or histidine (or glutamate/aspartate if included).

In some embodiments, the excipient to be limited or excluded is any excipient hereby disclosed in the disclosure (e.g., Table 2) not explicitly included. Accordingly, in some embodiments, the composition does not include more than 50 mM, 40 mM, 30 mM, 20 mM, 10 mM, 5 mM, 2 mM, 1 mM, 0.5 mM, 0.1 mM, 0.05 mM, 0.01 mM, 0.005 mM, or 0.001 mM of any excipient hereby disclosed in the disclosure (e.g., Table 2) not explicitly included. In some embodiments, the composition does not include any excipient hereby disclosed in the disclosure (e.g., Table 2) not explicitly included.

In some embodiments, the formulation includes one or more tonicity agents. The term "tonicity agent" as used herein denotes pharmaceutically acceptable agents used to modulate the tonicity of the formulation. Isotonicity generally relates to the osmotic pressure relative to a solution, usually relative to that of human blood serum. A formulation can be hypotonic, isotonic or hypertonic. In one aspect, the formulation is isotonic. An isotonic formulation is liquid or liquid reconstituted from a solid form, or suspension that solubilize up on dilation, e.g. from a lyophilized form and denotes a solution having the same tonicity as some other solution with which it is compared, such as physiologic salt solution and the blood serum. Suitable isotonicity agents include but are not limited to sodium chloride, potassium chloride, glycerin and any component from the group of amino acids, sugars, as defined herein as well as combinations thereof.

In some embodiments, the formulation includes one or more surfactants. As used herein, the term "surfactant" refers to a pharmaceutically acceptable organic substance having amphipathic structures; namely, it is composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical formulations and preparations of biological materials. In some embodiments of the pharmaceutical formulations described herein, the amount of surfactant is described as a percentage expressed in weight/volume percent (w/v %). Suitable pharmaceutically acceptable surfactants include but are not limited to the group of polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), or sodium dodecyl sulphate (SDS). Polyoxyethylenesorbitan-fatty acid esters include polysorbate 20, (sold under the trademark Tween 20™) and polysorbate 80 (sold under the trademark Tween 80™). Polyethylene-polypropylene copolymers include those sold under the names Pluronic® F68 or Poloxamer 188™. Polyoxyethylene alkyl ethers include those sold under the trademark Brij™. Alkylphenolpolyoxyethylene ethers include those sold under the tradename Triton-X.

In some embodiments, the formulation includes one or more lyoprotectants. A "lyoprotectant" refers to a pharmaceutically acceptable substance that stabilizes a protein during lyophilization (the process of rapid freezing and drying in a high vacuum). Examples of lyoprotectants include, without limitation, sucrose, trehalose or mannitol.

In some embodiments, the formulation further includes one or more antioxidants. An "antioxidant" refers to a molecule capable of slowing or preventing the oxidation of other molecules. Oxidation is a chemical reaction that transfers electrons from a substance to an oxidizing agent. Oxidation reactions can produce free radicals, which start chain reactions that destabilize the protein therapeutics and ultimately affect the product activity. Antioxidants terminate these chain reactions by removing free radical intermediates and inhibit other oxidation reactions by being oxidized themselves. As a result, antioxidants are often reducing agents, chelating agent and oxygen scavengers such as citrate, EDTA, DPTA, thiols, ascorbic acid or polyphenols. Non-limiting examples of antioxidants include ascorbic acid (AA, E300), thiosulfate, methionine, tocopherols (E306), propyl gallate (PG, E310), tertiary butylhydroquinone (TBHQ), butylated hydroxyanisole (BHA, E320) and butylated hydroxytoluene (BHT, E321).

In some embodiments, the formulation further includes one or more preservatives. A "preservative" is a natural or synthetic chemical that is added to products such as foods, pharmaceuticals, paints, biological samples, wood, etc. to prevent deformulation by microbial growth or by undesirable chemical changes. Preservative additives can be used alone or in conjunction with other methods of preservation. Preservatives may be antimicrobial preservatives, which inhibit the growth of bacteria and fungi, or antioxidants such as oxygen absorbers, which inhibit the oxidation of constituents. Common antimicrobial preservatives include, benzalkonium chloride, benzoic acid, cholorohexidine, glycerin, phenol, potassium sorbate, thimerosal, sulfites (sulfur dioxide, sodium bisulfite, potassium hydrogen sulfite, etc.) and disodium EDTA. Other preservatives include those commonly used in patenteral proteins such as benzyl alcohol, phenol, m-cresol, chlorobutanol or methylparaben.

In some embodiments, the formulation further includes one or more bulking agents. As used herein, the term "bulking agent" refers to an ingredient that provides bulk to a lyophilized formulation. Examples of bulking agents include, without limitation, mannitol, trehalose, lactose, sucrose, polyvinyl pyrrolidone, sucrose, glucose, glycine, cyclodextrins, dextran, solid PEGs and derivatives and mixtures thereof. In one embodiment, a formulation of the present disclosure optionally includes a bulking agent.

In some embodiment the formulation further includes buffering system such as citrate, acetate, borate, phosphate or combination of. In some embodiment the formulation further includes tertiary butanol to enhance property and stability of lyophilized material.

In some embodiment the formulation further includes viscosity lowering agent such as lysin, arginine, NaCl, glutamine, glycine or combinations thereof.

In some embodiments, the formulation can includes a controlled-release or stabilization polymer that may be selected from hyaluronic acid (HA), alginate, hydroxy methylcellulose (HPMC), hydroxy propylcellulose (HPC), sodium carboxymethyl cellulose (NaCMC); or povidones. Biodegradable matrices may comprise excipients such as, poly(D,L-lactic acid) (PLA), poly(D,L-lactic-co-glycolic acid) (PLGA), or a block copolymer comprising hydrophilic poly(ethylene glycol) (PEG) and one or more polymers selected from poly(lactic acid-co-glycolic acid) (PLGA), poly(ε-caprolactone) (PCL), and poly(ε-caprolactone-co-glycolic acid) (PCGA), such as poly(ε-caprolactone-co-glycolic acid)-poly(ethylene glycol)-poly(ε-caprolactone-co-glycolic acid) (PCGA-PEG-PCGA) and poly(lactic acid-co-glycolic acid)-poly(ethylene glycol)-poly(lactic acid-co-glycolic acid) (PLGA-PEG-PLGA) or a pharmaceutically acceptable salt thereof, or a combination thereof. In some embodiments, the formulation can include HSA (human serum albumin) or BSA (bovine serum albumin).

In some embodiments, the formulation (e.g., suspension) also includes suspending agent. The term "suspending agent" as used herein refers to a pharmaceutical acceptable excipient that promotes particle suspension or dispersion and reduces sedimentation. Suspending agents also act as thickening agents. They increase in viscosity of the solution, which is helpful to prevent sedimentation of the suspended particles. A suspension has well developed thixotropy. At rest the solution is sufficient viscous to prevent sedimentation and thus aggregation or caking of the particles. When agitation is applied the viscosity is reduced and provide good flow characteristic.

Non-limiting examples of types of suspending agents include polysaccharides, inorganic salts, and polymers. Specific examples of suspending agents include, without limitation, alginates, methylcellulose, hydroxyethylcellulose, carboxymethylcellulose, carboxymethylcellulose sodium, microcrystalline cellulose, acacia, tragacanth, xanthan gum, bentonite, carbomer, carageenan, powdered cellulose, gelatin, polyethylene glycol, povidone, dextrin, medium-chain triglycerides, sucrose, hydroxypropyl methyl cellulose, chistosan, polyoxyethylene, polyoxy-propylene ethers and combinations thereof.

In some embodiments, the suspending agent is selected from polyethylene glycol (e.g., polyethylene glycol 4000), carboxymethylcellulose sodium, methylcellulose, povidone, and combinations thereof. In one embodiment, the suspending agent is polyethylene glycol 4000. In another embodiment, the suspending agent is carboxymethylcellulose sodium.

The concentration of the suspending agent can generally be from about 0.1 mg/mL to about 200 mg/mL, or from about 0.5 mg/mL to about 100 mg/mL, from about 1 mg/mL to about 75 mg/mL, from about 5 mg/mL to about 60 mg/mL, from about 5 mg/mL to about 20 mg/mL, or from about 40 mg/mL to about 60 mg/mL. In some embodiments, concentration of the suspending agent is from about 0.1% (w/w) to about 7.5% (w/w), or from about 0.1% (w/w) to about 6% (w/w), from about 0.2% (w/w) to about 6% (w/w), from about 0.5% (w/w) to about 6% (w/w), from about 1% (w/w) to about 6% (w/w).

For polyethylene glycol 4000, the concentration can be from about 10 mg/mL to about 100 mg/mL, from about 25 mg/mL to about 75 mg/mL, from about 40 mg/mL to about 70 mg/mL, or from about 50 mg/mL to about 60 mg/mL. For carboxymethylcellulose sodium, the concentration can be from about 1 mg/mL to about 50 mg/mL, from about 2 mg/mL to about 30 mg/mL, from about 5 mg/mL to about 20 mg/mL, or from about 7 mg/mL to about 15 mg/mL. For methylcellulose, the concentration can be from about 0.1 mg/mL to about 10 mg/mL, from about 0.2 mg/mL to about 5 mg/mL, from about 0.5 mg/mL to about 2 mg/mL, or from about 0.75 mg/mL to about 1.25 mg/mL.

Example excipients that fall into one or more categories are illustrated in Table 2.

TABLE 2

Example Excipients

| Excipient | Role | Notes/representative conc |
|---|---|---|
| Acetate | Buffer/salt | 10-200 mM |
| Citrate | Buffer/salt | 10-200 mM |
| Tartrate | Buffer/salt | |
| Histidine | Buffer/salt | 5-50 mM |
| Glutamate | Buffer/salt | |
| Phosphate | Buffer/salt | |
| Tris | Buffer/salt | 10-200 mM |
| Glycine | Buffer/salt | |
| Bicarbonate | Buffer/salt | |
| Succinate | Buffer/salt | |
| Sulfate | Buffer/salt | |
| Nitrate | Buffer/salt | |
| Sodium Camphorsulfonate | Buffer/salt | 100-1000 mM |
| Trimethylphenylammonium Iodide | Buffer/salt | 100-1000 mM |
| MOPS (3-(N-morpholino)propanesulfonic acid) | Buffer/salt | 10-100 mM |
| NaCl | Buffer/salt | 100-1000 mM |
| Sodium Succinate | Buffer/salt | 20-500 mM |
| $CaCl_2$ | Buffer/salt | 2-50 mM |
| MgCl2 | Buffer/salt | 2-50 mM |
| Sodium Phosphate | Buffer/salt | 10-200 mM |
| Sodium Acetate | Buffer/salt | 10-200 mM |
| Sodium Citrate | Buffer/salt | 10-200 mM |
| Lactic acid | Buffer/salt | 20-200 mM |
| Malic acid | Buffer/salt | 20-200 mM |
| Mannitol | Tonicity agent | |
| Sorbitol | Tonicity agent | 2-15% (w/v) |
| Lactose | Tonicity agent | |
| Dextrose | Tonicity agent | |
| Trehalose | Tonicity agent | |
| Sodium Chloride | Tonicity agent | |
| Potassium Chloride | Tonicity agent | |

TABLE 2-continued

Example Excipients

| Excipient | Role | Notes/representative conc |
|---|---|---|
| Glycerol | Tonicity agent | 2-15% (w/v) |
| Glycerin | Tonicity agent | |
| Sucrose | Sugar/polyol | 1-8% (w/v) |
| Trehalose | Sugar/polyol | 50-300 mM |
| Glucose | Sugar/polyol | |
| Lactose | Sugar/polyol | 2-10% (w/v) |
| Sorbitol | Sugar/polyol | |
| Mannitol | Sugar/polyol | |
| Glycerol | Sugar/polyol | |
| Arginine | Amino acid | 20-120 mM |
| Aspartic Acid | Amino acid | 20-120 mM |
| Glutamic acid | Amino acid | 20-120 mM |
| Lysine | Amino acid | 20-120 mM |
| Proline | Amino acid | |
| Glycine | Amino acid | |
| Histidine | Amino acid | 10-100 mM |
| Methionine | Amino acid | 10-50 mM |
| Alanine | Amino acid | |
| Isoleucine | Amino acid | 10-50 mM |
| Tryptophan | Amino acid | 10-100 mM |
| Gelatin | Polymer/protein | |
| PVP | Polymer/protein | |
| PLGA | Polymer/protein | |
| Hydroxy methylcellulose (HPMC) | Polymer/protein | 1-10% (w/v) |
| PEG | Polymer/protein | |
| Dextran | Polymer/protein | |
| Cyclodextrin and derivatives | Polymer/protein | |
| Starch derivatives | Polymer/protein | |
| HSA (human serum albumin) | Polymer/protein | 5-50 mg/mL |
| BSA (bovine serum albumin) | Polymer/protein | 5-50 mg/mL |
| Polysorbate 20 (Tween 20) | Surfactant | 0.005-0.1% (w/v) |
| Polysorbate 80 (Tween 80) | Surfactant | 0.005-0.1% (w/v) |
| Poloxamer (Pluronic F68 and F127) | Surfactant | |
| Triton X-100 | Surfactant | |
| Brij 30 | Surfactant | 0.01-0.1% (w/v) |
| Brij 35 | Surfactant | 0.01-0.1% (w/v) |
| Histamine | Antioxidant/preservative | |
| Methionine | Antioxidant/preservative | |
| Ascorbic acid | Antioxidant/preservative | |
| Glutathione | Antioxidant/preservative | |
| Vitamin E | Antioxidant/preservative | |
| Poly(ethylenimine) | Antioxidant/preservative | |
| Benzyl alcohol | Preservative | |
| Metacresol | Preservative | |
| Phenol | Preservative | |
| 2-phenoxyethanol | Preservative | |
| Edetate disodium | Chelator/preservative | |
| Diethylenetria mine pentaacetic acid (DTPA) | Chelator/preservative | |
| Citric acid | Chelator/preservative | |
| Hexaphosphate | Chelator/preservative | |
| Thioglycolic acid | Chelator/preservative | |
| Zinc | Chelator/preservative | |

In some embodiments, histidine (e.g., histidine HCl) is present at a concentration of about 5-50 mM. In some embodiments, histidine's concentration is at least about 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, or 45 mM. In some embodiments, histidine's concentration is not higher than about 100 mM, 90 mM, 80 mM, 70 mM, 60 mM, 50 mM, 45 mM, 40 mM, 35 mM, 30 mM, 29 mM, 28 mM, 27 mM, 26 mM, 25 mM, 24 mM, 23 mM, 22 mM, 21 mM, 20 mM, 19 mM, 18 mM, 17 mM, 16 mM, or 15 mM. In some embodiments, histidine's concentration is about 5-40 mM, 5-35 mM, 5-30 mM, 5-25 mM, 5-20 mM, 10-50 mM, 10-45 mM, 10-40 mM, 10-35 mM, 10-30 mM, 10-25 mM, 10-20 mM, 15-50 mM, 15-45 mM, 15-40 mM, 15-35 mM, 15-30 mM, 15-25 mM, 15-20 mM, 20-50 mM, 20-45 mM, 20-40 mM, 20-35 mM, 20-30 mM, or 20-25 mM.

In some embodiments, arginine is present at a concentration of about 5-100 mM. In some embodiments, arginine's concentration is at least about 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, or 45 mM. In some embodiments, arginine's concentration is not higher than about 100 mM, 90 mM, 80 mM, 70 mM, 60 mM, 50 mM, 45 mM, 40 mM, 35 mM, 30 mM, 29 mM, 28 mM, 27 mM, 26 mM, 25 mM, 24 mM, 23 mM, 22 mM, 21 mM, 20 mM, 19 mM, 18 mM, 17 mM, 16 mM, or 15 mM. In some embodiments, arginine's concentration is about 5-40 mM, 5-35 mM, 5-30 mM, 5-25 mM, 5-20 mM, 10-50 mM, 10-45 mM, 10-40 mM, 10-35 mM, 10-30 mM, 10-25 mM, 10-20 mM, 15-50 mM, 15-45 mM, 15-40 mM, 15-35 mM, 15-30 mM, 15-25 mM, 15-20 mM, 20-50 mM, 20-45 mM, 20-40 mM, 20-35 mM, 20-30 mM, or 20-25 mM.

In some embodiments, lysine is present at a concentration of about 5-100 mM. In some embodiments, lysine's concentration is at least about 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, or 45 mM. In some embodiments, lysine's concentration is not higher than about 100 mM, 90 mM, 80 mM, 70 mM, 60 mM, 50 mM, 45 mM, 40 mM, 35 mM, 30 mM, 29 mM, 28 mM, 27 mM, 26 mM, 25 mM, 24 mM, 23 mM, 22 mM, 21 mM, 20 mM, 19 mM, 18 mM, 17 mM, 16 mM, or 15 mM. In some embodiments, lysine's concentration is about 5-40 mM, 5-35 mM, 5-30 mM, 5-25 mM, 5-20 mM, 10-50 mM, 10-45 mM, 10-40 mM, 10-35 mM, 10-30 mM, 10-25 mM, 10-20 mM, 15-50 mM, 15-45 mM, 15-40 mM, 15-35 mM, 15-30 mM, 15-25 mM, 15-20 mM, 20-50 mM, 20-45 mM, 20-40 mM, 20-35 mM, 20-30 mM, or 20-25 mM.

In some embodiments, trehalose (e.g., trehalose dihydrate) is present at a concentration of about 2%-20% (w/v). In some embodiments, trehalose's concentration is at least about 2%, 3%, 4%, 5%, 6%, 7%, 8%, 9%, 10%, 11%, 12%, 15%, 17% or 18% (w/v). In some embodiments, trehalose's concentration is not higher than about 20%, 19%, 18%, 17%, 16%, 15%, 14%, 13%, 12%, 11%, 10%, 9%, 8%, 7%, 6%, 5%, 4%, or 3% (w/v). In some embodiments, trehalose's concentration is about 2%-20%, 2%-19%, 2%-18%, 2%-17%, 2%-16%, 2%-15%, 2%-14%, 2%-13%, 2%-12%, 2%-11%, 2%-10%, 2%-9%, 2%-8%, 3%-20%, 3%-19%, 3%-18%, 3%-17%, 3%-16%, 3%-15%, 3%-14%, 3%-13%, 3%-13%, 3%-11%, 3%-10%, 3%-9%, 3%-8%, 4%-20%, 4%-19%, 4%-18%, 4%-17%, 4%-16%, 4%-15%, 4%-14%, 4%-13%, 4%-14%, 4%-11%, 4%-10%, 4%-9%, 4%-8%, 5%-20%, 5%-19%, 5%-18%, 5%-17%, 5%-16%, 5%-15%, 5%-14%, 5%-13%, 5%-15%, 5%-11%, 5%-10%, 5%-9%, 5%-8%, 6%-20%, 6%-19%, 6%-18%, 6%-17%, 6%-16%, 6%-16%, 6%-14%, 6%-13%, 6%-16%, 6%-11%, 6%-10%, 6%-9%, 6%-8%, 7%-20%, 7%-19%, 7%-18%, 7%-17%, 7%-17%, 7%-17%, 7%-14%, 7%-13%, 7%-17%, 7%-11%, 7%-10%, 7%-9%, 7%-8%, 8%-20%, 8%-19%, 8%-18%, 8%-18%, 8%-18%, 8%-18%, 8%-14%, 8%-13%, 8%-18%, 8%-11%, 8%-10%, 8%-9%, 9%-20%, 9%-19%, 9%-18%, 9%-19%, 9%-19%, 9%-19%, 9%-14%, 9%-13%, 9%-19%, 9%-11%, 9%-10%, 10%-20%, 10%-19%, 10%-18%, 10%-110%, 10%-110%, 10%-110%, 10%-14%, 10%-13%, 10%-110%, or 10%-11% (w/v).

In some embodiments, sucrose is present at a concentration of about 2%-20% (w/v). In some embodiments, sucrose's concentration is at least about 2%, 3%, 4%, 5%, 6%, 7%, 8%, 9%, 10%, 11%, 12%, 15%, 17% or 18% (w/v). In some embodiments, sucrose's concentration is not higher than about 20%, 19%, 18%, 17%, 16%, 15%, 14%, 13%, 12%, 11%, 10%, 9%, 8%, 7%, 6%, 5%, 4%, or 3% (w/v). In some embodiments, sucrose's concentration is about 2%-20%, 2%-19%, 2%-18%, 2%-17%, 2%-16%, 2%-15%, 2%-14%, 2%-13%, 2%-12%, 2%-11%, 2%-10%, 2%-9%, 2%-8%, 3%-20%, 3%-19%, 3%-18%, 3%-17%, 3%-16%, 3%-15%, 3%-14%, 3%-13%, 3%-13%, 3%-11%, 3%-10%, 3%-9%, 3%-8%, 4%-20%, 4%-19%, 4%-18%, 4%-17%, 4%-16%, 4%-15%, 4%-14%, 4%-13%, 4%-14%, 4%-11%, 4%-10%, 4%-9%, 4%-8%, 5%-20%, 5%-19%, 5%-18%, 5%-17%, 5%-16%, 5%-15%, 5%-14%, 5%-13%, 5%-15%, 5%-11%, 5%-10%, 5%-9%, 5%-8%, 6%-20%, 6%-19%, 6%-18%, 6%-17%, 6%-16%, 6%-16%, 6%-14%, 6%-13%, 6%-16%, 6%-11%, 6%-10%, 6%-9%, 6%-8%, 7%-20%, 7%-19%, 7%-18%, 7%-17%, 7%-17%, 7%-17%, 7%-14%, 7%-13%, 7%-17%, 7%-11%, 7%-10%, 7%-9%, 7%-8%, 8%-20%, 8%-19%, 8%-18%, 8%-18%, 8%-18%, 8%-18%, 8%-14%, 8%-13%, 8%-18%, 8%-11%, 8%-10%, 8%-9%, 9%-20%, 9%-19%, 9%-18%, 9%-19%, 9%-19%, 9%-19%, 9%-14%, 9%-13%, 9%-19%, 9%-11%, 9%-10%, 10%-20%, 10%-19%, 10%-18%, 10%-110%, 10%-110%, 10%-110%, 10%-14%, 10%-13%, 10%-110%, or 10%-11% (w/v).

In some embodiments, NaCl is present at a concentration of about 5-200 mM. In some embodiments, NaCl's concentration is at least about 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 60 mM, 70 mM, 80 mM, 90 mM, 100 mM, 120 mM, 140 mM or 150 mM. In some embodiments, NaCl's concentration is not higher than about 200 mM, 180 mM, 150 mM, 120 mM, 100 mM, 90 mM, 80 mM, 70 mM, 60 mM, or 50 mM.

In some embodiments, $MgCl_2$ is present at a concentration of about 5-50 mM. In some embodiments, $MgCl_2$'s concentration is at least about 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, or 45 mM. In some embodiments, $MgCl_2$'s concentration is not higher than about 100 mM, 90 mM, 80 mM, 70 mM, 60 mM, 50 mM, 45 mM, 40 mM, 35 mM, 30 mM, 29 mM, 28 mM, 27 mM, 26 mM, 25 mM, 24 mM, 23 mM, 22 mM, 21 mM, 20 mM, 19 mM, 18 mM, 17 mM, 16 mM, or 15 mM. In some embodiments, $MgCl_2$'s concentration is about 5-40 mM, 5-35 mM, 5-30 mM, 5-25 mM, 5-20 mM, 10-50 mM, 10-45 mM, 10-40 mM, 10-35 mM, 10-30 mM, 10-25 mM, 10-20 mM, 15-50 mM, 15-45 mM, 15-40 mM, 15-35 mM, 15-30 mM, 15-25 mM, 15-20 mM, 20-50 mM, 20-45 mM, 20-40 mM, 20-35 mM, 20-30 mM, or 20-25 mM.

In some embodiments, Sodium Camphorsulfonate is present at a concentration of about 5-200 mM. In some embodiments, Sodium Camphorsulfonate's concentration is at least about 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 60 mM, 70 mM, 80 mM, 90 mM, 100 mM, 120 mM, 140 mM or 150 mM. In some embodiments, Sodium Camphorsulfonate's concentration is not higher than about 200 mM, 180 mM, 150 mM, 120 mM, 100 mM, 90 mM, 80 mM, 70 mM, 60 mM, or 50 mM.

In some embodiments, polysorbate 80 (PS80) is present at a concentration of about 0.015%-0.05% (w/v). In some embodiments, PS80 is present at a concentration of at least about 0.015%, 0.016%, 0.017%, 0.018%, 0.019%, 0.02%, 0.021%, 0.022%, 0.023%, 0.024%, 0.025%, 0.026%, 0.027%, 0.028%, 0.029%, or 0.03% (w/v). In some embodiments, PS80 is present at a concentration of not higher than 0.05%, 0.049%, 0.048%, 0.047%, 0.046%, 0.045%, 0.044%, 0.043%, 0.042%, 0.041%, 0.04%, 0.039%, 0.038%, 0.037%, 0.036%, 0.035%, 0.034%, 0.033%, 0.032%, 0.031%, 0.03%, 0.029%, 0.028%, 0.027%, 0.026%, 0.025%, 0.024%, 0.023%, 0.022%, 0.021%, or 0.02% (w/v).

In some embodiments, polysorbate 20 (PS20) is present at a concentration of about 0.015%-0.05% (w/v). In some embodiments, PS80 is present at a concentration of at least about 0.015%, 0.016%, 0.017%, 0.018%, 0.019%, 0.02%, 0.021%, 0.022%, 0.023%, 0.024%, 0.025%, 0.026%, 0.027%, 0.028%, 0.029%, or 0.03% (w/v). In some embodiments, PS80 is present at a concentration of not higher than 0.05%, 0.049%, 0.048%, 0.047%, 0.046%, 0.045%, 0.044%, 0.043%, 0.042%, 0.041%, 0.04%, 0.039%, 0.038%, 0.037%, 0.036%, 0.035%, 0.034%, 0.033%, 0.032%, 0.031%, 0.03%, 0.029%, 0.028%, 0.027%, 0.026%, 0.025%, 0.024%, 0.023%, 0.022%, 0.021%, or 0.02% (w/v).

In some embodiments, hydroxy methylcellulose (HPMC) is present at a concentration of about 1%-10% (w/v). In some embodiments, HPMC's concentration is at least about 1%, 2%, 3%, 4%, 5%, 6%, 7%, 8%, or 9% (w/v). In some embodiments, HPMC's concentration is not higher than about 10%, 9%, 8%, 7%, 6%, 5%, 4%, or 3% (w/v).

In some embodiments, HSA (human serum albumin) or BSA (bovine serum albumin) is present at a concentration of about 5-50 mg/mL. In some embodiments, the albumin's concentration is at least about 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 25 mg/mL, 30 mg/mL, 35 mg/mL, 40 mg/mL, or 45 mg/mL. In some embodiments, the albumin's concentration is not higher than about 100 mg/mL, 90 mg/mL, 80 mg/mL, 70 mg/mL, 60 mg/mL, 50 mg/mL, 45 mg/mL, 40 mg/mL, 35 mg/mL, 30 mg/mL, 29 mg/mL, 28 mg/mL, 27 mg/mL, 26 mg/mL, 25 mg/mL, 24 mg/mL, 23 mg/mL, 22 mg/mL, 21 mg/mL, 20 mg/mL, 19 mg/mL, 18 mg/mL, 17 mg/mL, 16 mg/mL, or 15 mg/mL. In some embodiments, the albumin's concentration is about 5-40 mg/mL, 5-35 mg/mL, 5-30 mg/mL, 5-25 mg/mL, 5-20 mg/mL, 10-50 mg/mL, 10-45 mg/mL, 10-40 mg/mL, 10-35 mg/mL, 10-30 mg/mL, 10-25 mg/mL, 10-20 mg/mL, 15-50 mg/mL, 15-45 mg/mL, 15-40 mg/mL, 15-35 mg/mL, 15-30 mg/mL, 15-25 mg/mL, 15-20 mg/mL, 20-50 mg/mL, 20-45 mg/mL, 20-40 mg/mL, 20-35 mg/mL, 20-30 mg/mL, or 20-25 mg/mL.

In some embodiments, the composition has a pH of 5-8. In some embodiments, the pH is not lower than 5, 5.4, 5.5, 5.6, 5.8, 5.9, 6, 6.1, 6.4, 6.5, 6.6, 6.8, 6.9, 7, 7.1, 7.2, 7.4, 7.5, 7.6, 7.8, or 7.9. In some embodiments, the pH is not higher than 8, 7.9, 7.8, 7.6, 7.5, 7.4, 7.2, 7.1, 7, 6.9, 6.8, 6.6, 6.5, 6.4, 6.3, 6.2, 6.15, 6.1, 6.05, 6, 5.95, 5.9, 5.85, or 5.8.

In some embodiments, the formulation includes combinations as shown in Table 3.

TABLE 3

Example Combinations of Excipients in Formulation

| Combination | Notes/representative concentrations (for illustration purpose) |
|---|---|
| NaCl/Arginine | 150 mM/50mM |
| NaCl/MgCl$_2$ | 150 mM/10 mM |
| NaCl/MgCl$_2$/Arginine | 150 mM/10 mM/50 mM |
| Sucrose/Arginine | 10%/50 mM |
| Sucrose/MgCl$_2$ | 10%/10 mM |
| Sucrose/MgCl$_2$/Arginine | 10%/10 mM/50 mM |
| Sucrose/NaCl/Arginine | 5%/75 mM/50 mM |
| Sucrose/NaCl/MgCl$_2$ | 5%/75 mM/10 mM |
| Sucrose/NaCl/Arginine/MgCl$_2$ | 5%/75 mM/50 mM/10 mM |
| NaCl/Lysine | 150 mM/50 mM |
| NaCl/MgCl$_2$/Lysine | 150 mM/10 mM/50 mM |
| Sucrose/Lysine | 10%/50 mM |
| Sucrose/MgCl$_2$/Lysine | 10%/10 mM/50 mM |
| Sucrose/NaCl/Lysine | 5%/75 mM/50 mM |
| Sucrose/NaCl/Lysine/MgCl$_2$ | 5%/75 mM/50 mM/10 mM |
| Histidine/NaCl/Arginine | 10 mM/75 mM/50 mM |
| Histidine/Arginine | 80 mM/50 mM |
| Histidine/NaCl/Lysine | 10 mM/75 mM/50 mM |
| Histidine/Lysine | 80 mM/50 mM |
| Sucrose/Histidine/Arginine | 3%/50 mM/50 mM |
| Mannitol/Sucrose/Histidine/Arginine | 5%/1%/50 mM/50 mM |
| Mannitol/Sucrose/Histidine/Arginine/PS20 | 5%/1%/50 mM/50 mM/0.01% |

TABLE 3-continued

Example Combinations of Excipients in Formulation

| Combination | Notes/representative concentrations (for illustration purpose) |
|---|---|
| Succinate/Sucrose/Mannitol/Arginine | 50 mM/3%/5%/50 mM |
| Histidine/Sucrose/Mannitol/Arginine | 50 mM/3%/5%/50 mM |
| MOPS/Sucrose/Arginine | 50 mM/3%/50 mM |
| Tris/Sucrose/Mannitol/Arginine | 50 mM/3%//5%/50 mM |
| Sodium Phosphate/Sucrose/Mannitol/Arginine | 50 mM/3%/5%/50 mM |
| Sucrose/Histidine/Arginine | 1%/50 mM/50 mM |
| Sucrose/Histidine/Arginine/Mannitol | 1%/50 mM/50 mM/S% |
| Sucrose/Histidine/Arginine/Glycine | 1%/50 mM/50 mM/2% |
| Trehalose/Histidine/Arginine/Mannitol | 3%/50 mM/50 mM/5% |
| Sucrose/Histidine/Arginine/PS20 | 6%/100 mM/100 mM/0.01% |
| Sodium Phosphate/Sucrose/Mannitol | 5 mM/3%/5% |

In some embodiments, the aqueous formulations includes emactuzumab at a concentration that is at least about 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, or even 250 mg/mL. In some embodiments, the concentration is not higher than about 500 mg/mL, 400 mg/mL, or 300 mg/mL.

In some embodiments, the aqueous formulations includes lacnotuzumab at a concentration that is at least about 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, or even 250 mg/mL. In some embodiments, the concentration is not higher than about 500 mg/mL, 400 mg/mL, or 300 mg/mL.

In some embodiments, the aqueous formulations includes AM001 at a concentration that is at least about 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, or even 250 mg/mL. In some embodiments, the concentration is not higher than about 500 mg/mL, 400 mg/mL, or 300 mg/mL.

In some embodiments, the aqueous formulations include axatilimab at a concentration that is at least about 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, or even 250 mg/mL. In some embodiments, the concentration is not higher than about 500 mg/mL, 400 mg/mL, or 300 mg/mL.

In some embodiments, the aqueous formulations include cabiralizumab at a concentration that is at least about 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, or even 250 mg/mL. In some embodiments, the concentration is not higher than about 500 mg/mL, 400 mg/mL, or 300 mg/mL.

In some embodiments, the aqueous formulations include PD-0360324 at a concentration that is at least about 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, or even 250 mg/mL. In some embodiments, the concentration is not higher than about 500 mg/mL, 400 mg/mL, or 300 mg/mL.

Table 4 below illustrates a few formulations for AM001, which can also be used for other disclosed antibodies.

TABLE 4

Example Formulations

| Ingredients | Amount (mg/mL) | Range |
|---|---|---|
| Formulation Example 1: | | |
| MAB (E.G., AM001) | 150 | 140-210 |
| Citric acid monohydrate | 4.1 | 3-5 |
| Histidine | 8.1 | 6-10 |
| IN Sodium hydroxide to adjust pH | 1N to adjust pH to 5.0 | 4.8-5.2 |
| Arginine | 10.2 | 8-12 |
| Water for injection USP | QS | QS |
| Formulation Example 2: | | |
| MAB (E.G., AM001) | 140 | 120-210 |
| Citric acid monohydrate | 4.1 | 3-5 |
| Histidine | 16.72 | 10-20 |
| IN Sodium hydroxide to adjust pH | 1N to adjust pH to 5.0 | 4.8-5.2 |
| Arginine | 10.2 | 8-12 |
| Water for injection USP | QS | QS |
| Formulation Example 3: | | |
| MAB (E.G., AM001) | 150 | 140-210 |
| Acetic acid | 3.71 | 3-5 |
| Histidine | 8.1 | 6-10 |
| IN Sodium hydroxide to adjust pH | 1N to adjust pH to 5.0 | 4.8-5.2 |
| Arginine | 10.2 | 8-12 |
| Polysorbate 20 | 2.28 | 1-5 |
| Water for injection USP | QS | QS |
| Formulation Example 4: | | |
| MAB (E.G., AM001) | 150 | 140-210 |
| L Histidine HCL | 9.7 | 5-15 |
| L-Histidine | 8.1 | 6-10 |
| IN Sodium hydroxide to adjust pH | 1N to adjust pH to 5.0 | 4.8-5.2 |
| Arginine | 10.2 | 8-12 |
| Polysorbate 20 | 2.28 | 1-5 |
| Water for injection USP | QS | QS |
| Formulation Example 5: | | |
| MAB (E.G., AM001) | 175 | 140-210 |
| L Histidine HCL Monohydrate | 3.93 | 3-5 |
| L-Histidine | 8.1 | 6-10 |
| IN Sodium hydroxide to adjust pH | 1N to adjust pH to 5.0 | 4.8-5.2 |
| Arginine | 10.2 | 8-12 |
| Polysorbate 80 | 0.5 | 0.2-1 |
| Sucrose | 9.1 | 7-12 |
| Water for injection USP | QS | QS |
| Formulation Example 6: | | |
| MAB (E.G., AM001) | 150 | 140-210 |
| L Histidine HCL | 9.7 | 7-13 |
| Proline | 16 | 12-20 |
| IN Sodium hydroxide to adjust pH | 1N to adjust pH to 5.0 | 4.8-5.2 |
| Glutamic acid | 6.5 | 5-8 |
| Polysorbate 20 | 2.28 | 1-5 |
| Water for injection USP | QS | QS |
| Formulation Example 7: | | |
| MAB (E.G., AM001) | 160 | 140-210 |
| L Histidine HCL | 9.7 | 7-13 |
| L-Histidine | 3.1 | 1-5 |
| IN Sodium hydroxide to adjust pH | 1N to adjust pH to 5.0 | 4.8-5.2 |
| Arginine | 26.2 | 20-35 |
| Poloxamer 188 | 0.5 | 0.2-0.8 |
| L-Aspartic acid | pH adjustment to pH 5 | pH adjustment |
| Water for injection USP | QS | QS |
| Formulation Example 8: | | |
| MAB (E.G., AM001) | 180 | 140-210 |
| L Histidine HCL | 9.7 | 7-13 |
| L-Histidine | 8.1 | 6-10 |
| IN Sodium hydroxide to adjust pH | 1N to adjust pH to 5.0 | 4.8-5.2 |
| Glycine | 10.2 | 8-12 |
| Polysorbate 80 | 4.2 | 2-6 |
| Water for injection USP | QS | QS |
| Formulation Example 9: | | |
| MAB (E.G., AM001) | 150 | 140-210 |
| α-α-trehalose | 397 | 200-600 |
| L-Histidine | 7.5 | 6-9 |
| L-Histidine HCL monohydrate | 50.5 | 30-80 |
| Sucrose | 90 | 6-12 |
| Polysorbate 20 | 1.8 | 0.5-3 |
| L Methionine | 22.4 | 10-30 |
| Water for injection USP | QS | QS |
| Formulation Example 10: | | |
| MAB (E.G., AM001) | 150 | 140-210 |
| α-α-trehalose | 290 | 200-400 |
| Mannitol | 210 | 150-280 |
| L-Arginine | 25 | 10-40 |
| Acetic acid | 3.7 | 2-5 |
| Polysorbate 20 | 8 | 6-10 |
| 1N Sodium Hydroxide | pH adjustment to 5 | pH adjustment to 4.8-5.2 |
| Water for injection USP | QS | QS |
| Formulation Example 11: | | |
| MAB (E.G., AM001) | 160 | 140-210 |
| α-α-trehalose | 397 | 200-600 |
| L-Histidine | 15.5 | 10-20 |
| L-Histidine HCL monohydrate | 40.5 | 430-50 |
| Arginine | 59 | 40-80 |
| Polysorbate 20 | 0.6 | 0.2-1 |
| Water for injection USP | QS | QS |
| Formulation Example 12: | | |
| MAB (E.G., AM001) | 150 | 140-210 |
| Sodium Phosphate dibasic | 5.3 | 3-8 |
| Citric acid monohydrate | 7.5 | 5-10 |
| Hydroxypropyl methylcellulose | 1.5 | 0.5-4 |
| Sucrose | 90 | 60-120 |
| Polysorbate 80 | 0.1 | 0.5-2 |
| Sodium Chloride | 53 | 40-70 |
| Water for injection USP | QS | QS |
| Formulation Example 13: | | |
| MAB (E.G., AM001) | 70 | 50-150 |
| Sucrose | 90 | 60-120 |
| Polysorbate 20 | 0.04 | 0.01-0.1 |
| Acetic acid | 10 mM | 5-20 mM |
| IN Sodium Hydroxide | To adjust pH 4.9-5.5 | To adjust pH 4.9-5.5 |
| Water for injection USP | QS | QS |

Also provided, in some embodiments, is a lyophilized composition that can be prepared by freeze-drying the aqueous solution as disclosed herein. In some embodiments, also provided is a solution that can be prepared by dissolving the lyophilized composition in a solvent such as water.

III. Methods of Using the Formulations

Methods of using the disclosed formulations/compositions are also provided. In some embodiments, the methods are for treating a patient having TGCT or other tumors (e.g., melanoma, glioblastoma, leukemia, and congenital hypertrichosis lanuginosa (CHL)) that can be suitably treated with CSF1/CSF1R inhibition.

The present disclosure relates to pharmaceutical compositions for treating chronic diseases, such as tenosynovial giant cell tumor (TGCT), pigmented villonodular synovitis (PVNS) and rheumatoid arthritis (RA), by local administration, and methods for preparing and using the compositions.

Tenosynovial giant cell tumor (TGCT) is a neoplasm derived from the synovium that causes recruitment of immune cells, specifically macrophages, leading to formation of a mass. These tumors are often classified by their growth pattern (localized or diffuse) and site (intra- or extra-articular). See, e.g., Giustini et al., *Clinical Sarcoma Research*, 2018 (8):14.

Localized TGCT is characterized by a discrete nodule. While any location is possible, localized forms mainly involve the digits joints and wrist (85% of cases); foot and ankle, knee, hip or other joint locations are more rare. Diffuse forms mainly involve the large joints: knee, hip, ankle and elbow. Localized forms are systematically benign; diffuse forms are more aggressive and destructive, and may exceptionally include a malignant component.

Pigmented villonodular synovitis (PVNS), also known as diffuse TGCT (D-TGCT), is characterized by a diffuse proliferation in the synovium, commonly occurring in and around the hip or knee. Local and diffuse disease may occur intra-articularly throughout the body. PVNS can also be extra-articular, and, in rare circumstances, can metastasize to adjacent lymph nodes and the lungs.

Current treatment options for TGCT are limited, including surgery and radiotherapy. Surgery is often the treatment of choice for patients with TGCT/PVNS. Localized TGCT/PVNS is managed by marginal excision. Recurrences occur in 8-20% of patients and are managed by re-excision. Diffuse TGCT/PVNS tends to recur more often (33-50%) and has a much more aggressive clinical course. Patients are often symptomatic and require multiple surgical procedures during their lifetime. In some cases, the joint may need to be replaced. See, e.g., Palmerini et al., *Expert opinion on Orphan Drugs*, 2018 (6)12:753-7. The formulations disclosed herein are suitable for treating TGCT.

In some embodiments, the composition is administered subcutaneously. In some embodiments, the composition is administered intramuscularly or intravitreally. In some embodiments, the composition is administered intravenously. In some embodiments, the composition is administered intraarticularly.

In some embodiments, the administration is local or proximate to the site of the disease (e.g., TGCT). In some embodiments, the administration is intratumoral or at a site proximate to the tumor.

In some embodiments, TGCT is in a hand. In some embodiments, TGCT is in a knee. In some embodiments, TGCT is in a digit joint. In some embodiments, TGCT is in a wrist. In some embodiments, TGCT is in a foot. In some embodiments, TGCT is in a hip. In some embodiments, TGCT is in an elbow. In some embodiments, TGCT is in an ankle.

Another type of disease that can be suitably treated with the presently disclosed compositions is idiopathic pulmonary fibrosis (IPF). Idiopathic pulmonary fibrosis (IPF) is a serious chronic disease that affects the tissue surrounding the air sacs, or alveoli, in the lung. This condition occurs when that lung tissue becomes thick and stiff for unknown reasons. Over time, these changes can cause permanent scarring in the lungs, called fibrosis, that make it progressively more difficult to breathe.

In some embodiments, the composition is administered subcutaneously. In some embodiments, the composition is administered intramuscularly or intravitreally. In some embodiments, the composition is administered intravenously.

Yet another type of diseases that can be suitably treated with the presently disclosed compositions is polycystic kidney disease (PKD). PKD is the most common genetic disorder of the kidney characterized by the development of bilateral tubular cysts and the development of interstitial fibrosis. PKD refers to two separate genetic entities, Autosomal recessive polycystic kidney disease (ARPKD), which belongs to a group of congenital hepatorenal fibrocystic syndromes and autosomal dominant polycystic kidney disease (ADPKD). ARPKD is a rare dual organ disease commonly diagnosed in utero or at birth and occurs at a frequency of 1:20,000 live births.

In some embodiments, the composition is administered subcutaneously. In some embodiments, the composition is administered intramuscularly or intravitreally. In some embodiments, the composition is administered intravenously.

Still another class of diseases that can be suitably treated with the presently disclosed compositions are ocular diseases. In some embodiments, the administration is topical, ophthalmic, or local injection to the eye or nearby tissue.

In some embodiments, the formulations described herein are provided in an amount sufficient to provide a therapeutically effective amount of the therapeutic agent. In some embodiments, the administration is about once every month. In some embodiments, the administration (e.g., subcutaneous injection) is about once every week. In some embodiments, the administration is about once every 5 days, or every 4 days, every 3 days, every 2 days, or each day.

EXAMPLES

The disclosure is further understood by reference to the following examples, which are intended to be purely exemplary of the disclosure. The present disclosure is not limited in scope by the exemplified embodiments, which are intended as illustrations of single aspects of the disclosure only. Any methods that are functionally equivalent are within the scope of the disclosure. Various modifications of the disclosure in addition to those described herein will become apparent to those skilled in the art from the foregoing description and accompanying figures. Such modifications fall within the scope of the appended claims.

Example 1. In Vivo Exposure of AM001

This example measured the serum concentrations of anti-CSF1R antibody AM001 following subcutaneous administration. With the measurements, a desirable dosing schedule was estimated.

A single dose of AM001 (70 mg/mL) was administered to cynomolgus monkeys via subcutaneous (s.c.) injection (10 mg/Kg×3 monkeys). Each day following the administration, serum concentration of the antibody was measured. The data are plotted in FIG. 1, and PK parameters summarized in the table below.

| PK Parameter | 10 mg/Kg S.C. Mean | 10 mg/Kg S.C. SD |
|---|---|---|
| $C_{max}$ (µg/mL) | 82.5 | 27.5 |
| $T_{max}$ (days) | 1.8 | 1 |
| $AUC_{last}$ (µg * days/mL) | 495 | 113 |

Absolute bioavailability was approximately 62%. Interestingly, the median $T_{max}$ of 1.25 days is unusually shorter than generally observed with human monoclonal antibodies in humans or monkeys (J T Ryman & B Meibohm, Pharmacokinetics of Monoclonal Antibodies, CPT Pharmacometrics Syst Pharmacol. 2017 6(9): 576-588; K W Walker et al., Pharmacokinetic comparison of a diverse panel of non-targeting human antibodies as matched IgG1 and IgG2 isotypes in rodents and non-human primates, PLoS ONE 2019, 14(5): e0217061).

Figure 2:
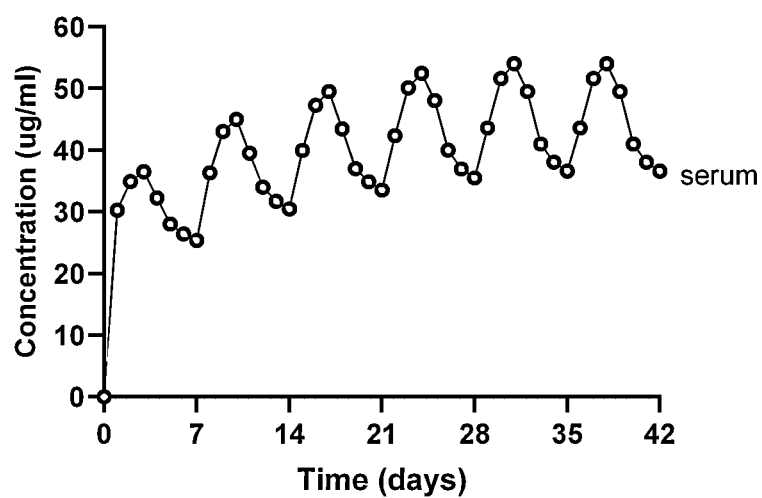
FIG. 2 shows projected serum concentration vs. time profile for weekly subcutaneous dosing in humans.

The data were extrapolated to a projected serum concentration vs. time profile for weekly s.c. dosing in humans (70 Kg) at 3 mg/Kg which should provide an efficacious exposure for various potential indications, such as TGCT (FIG. 2).

If the required dose (i.e., 210 mg) needs to be administered once s.c., assuming no more than 1.5 mL can be injected, the minimum drug concentration should be 140 mg/mL. If only 1 mL can be injected, the minimum drug concentration should be 210 mg/mL. For a twice daily s.c. injection, each time with 1 mL, then the minimum concentration should be 105 mg/mL.

Example 2. Sample Preparation for Formulation Development for AM001

This example tested multiple designed high-concentration formulations for AM001 for their physical stability, chemical stability and viscosity. Higher stability and lower viscosity are desired for the ultimate high concentration formulation.

Sample Preparation

Stock solutions of the drug substance (DS) AM001 were provided as 70 mg/mL AM001 in 10 mM acetate (pH 5.2), 9% (w/v) sucrose, and 0.004% (w/v) PS 20.

Diafiltration and Concentration of DS (AM001) with TFF

Tangential flow filtration (TFF) was conducted using a Millipore Cogent μScale system to both diafilter and concentrate the DS prior to dialysis. Prior to conducting diafiltration, the DS was allowed to warm to room temperature and diluted to ~35 mg/mL with 20 mM histidine (pH 5.3) buffer. Histidine buffer was utilized for this step, as it was found to reduce viscosity of AM001 versus several other buffers (acetate and citrate) examined in a pilot screening study conducted at pH 5.1-5.5.

Diluted DS was diafiltered with 5 diavolumes of 20 mM histidine (pH 5.3) buffer using a pump speed of 30%, a stir rate (for the retentate) of 30%, and a trans-membrane pressure (TMP) of ~15 psi. Following diafiltration, material was concentrated to ~160 mg/mL, and then recovered from the TFF system (in a 120 mL polycarbonate bottle) using a 5% pump speed. The solution was then loaded into 15 mL centrifugal spin concentrators and spun at 4000×g (20° C.) in 20-minute intervals until concentrated to ~170 mg/mL.

Dialysis Procedure

Formulations were prepared by dialyzing concentrated, diafiltered DS (~170 mg/mL) against the formulation placebo (i.e., buffer and tonicity modifiers/stabilizers) using Slide-A-Lyzer Mini Dialysis devices (20 kD MWCO, 2 mL capacity). Each formulation (bulk material) was sterile filtered using a Millipore Millex-GV syringe filter (0.22 μm). After filtration, the formulation was aliquoted at 0.5 mL into 1 mL Type 1 glass vials, stoppered (13 mm rubber stopper), and sealed with crimped aluminum caps. Sterile filtering and aliquoting was conducted in a biosafety cabinet using materials (i.e., vials, stoppers, etc.) which had been previously sterilized.

Protein concentration was determined using a SoloVPE instrument (C Technologies, Inc.; Bridgewater, N.J.). Concentration was calculated from absorbance at 280 nm using an extinction coefficient of 1.58 mL/(mg*cm). The absorbance measurement at 280 nm was corrected for scattering by utilizing a 320 and 350 nm correction.

Example 3. Initial Investigation of pH, Buffer Species and Viscosity Modifying Excipients This example investigated stability of AM001 as a function of pH, buffer species, and viscosity modifying excipient.

The tested pH range was 4.5-6.5. The evaluations were carried out after storage at 1 week 40° C., 2 weeks 25° C., and 4 weeks 5° C. Each sample (Table A1) was evaluated for physical stability using size exclusion chromatography and chemical stability using cation exchange chromatography. Each sample was checked for viscosity at time-zero. Visual assessments were conducted at all time-points.

TABLE A1

Listing of Tested Formulation Samples (F1-F17)

| No. | Protein (mg/mL) | pH | Acetate (mM) | Succinate (mM) | Citrate (mM) | Histidine (mM) | NaCl (mM) | Sorbitol (mM) |
| --- | --- | --- | --- | --- | --- | --- | --- | --- |
| F1 | 150 | 4.5 | 10 | 0 | 0 | 0 | 150 | 0 |
| F2 | 150 | 4.5 | 0 | 20 | 0 | 0 | 0 | 175 |
| F3 | 150 | 5 | 20 | 0 | 0 | 0 | 120 | 0 |
| F4 | 150 | 5 | 0 | 10 | 0 | 0 | 100 | 0 |
| F5 | 150 | 5 | 0 | 0 | 0 | 20 | 50 | 0 |
| F6 | 150 | 5 | 0 | 0 | 20 | 0 | 0 | 175 |
| F7 | 150 | 5 | 0 | 0 | 20 | 0 | 100 | 0 |
| F8 | 150 | 5.5 | 20 | 0 | 0 | 0 | 0 | 175 |
| F9 | 150 | 5.5 | 0 | 0 | 0 | 40 | 50 | 175 |
| F10 | 150 | 5.5 | 0 | 0 | 0 | 20 | 0 | 0 |
| F11 | 150 | 5.5 | 0 | 0 | 0 | 20 | 0 | 0 |
| F12 | 150 | 5.5 | 0 | 20 | 0 | 0 | 150 | 0 |
| F13 | 150 | 5.5 | 10 | 0 | 0 | 0 | 0 | 0 |
| F14 | 150 | 6 | 0 | 0 | 0 | 20 | 0 | 0 |
| F15 | 150 | 6 | 0 | 0 | 20 | 0 | 150 | 0 |
| F16 | 150 | 6.5 | 0 | 0 | 0 | 20 | 150 | 0 |
| F17 | 70 | 5.2 | 10 | 0 | 0 | 0 | 0 | 0 |

TABLE A1-continued

| | Listing of Tested Formulation Samples (F1-F17) | | | | | |
|---|---|---|---|---|---|---|
| No. | Arg * HCl (mM) | Lys * HCl (mM) | Arg * Glu (mM) | Proline (mM) | Sucrose (mM) | PS20 (%, w/v) |
| F1 | 0 | 0 | 0 | 0 | 0 | 0.009 |
| F2 | 50 | 0 | 0 | 0 | 0 | 0.009 |
| F3 | 25 | 0 | 0 | 0 | 0 | 0.009 |
| F4 | 0 | 50 | 0 | 0 | 0 | 0.009 |
| F5 | 0 | 0 | 0 | 175 | 0 | 0.009 |
| F6 | 0 | 0 | 50 | 0 | 0 | 0.009 |
| F7 | 50 | 0 | 0 | 0 | 0 | 0.009 |
| F8 | 0 | 50 | 0 | 0 | 0 | 0.009 |
| F9 | 0 | 0 | 0 | 0 | 0 | 0.009 |
| F10 | 150 | 0 | 0 | 0 | 0 | 0.009 |
| F11 | 0 | 0 | 0 | 270 | 0 | 0.009 |
| F12 | 0 | 0 | 0 | 0 | 0 | 0.009 |
| F13 | 0 | 0 | 0 | 0 | 260 | 0.009 |
| F14 | 0 | 0 | 150 | 0 | 0 | 0.009 |
| F15 | 0 | 0 | 0 | 0 | 0 | 0.009 |
| F16 | 0 | 0 | 0 | 0 | 0 | 0.009 |
| F17 | 0 | 0 | 0 | 0 | 260 | 0.004 |

*F17 is the stock solution

Visual Observations

Opalescence was evident in most formulations and was affected by excipient type and concentration. Formulations with NaCl had the most opalescence. Formulations with 150 mM Arg*HCl (F10) and Arg/Glu (F14) had some opalescence, but it was much less pronounced than formulations with NaCl. Formulations with a high percentage of polyol, sucrose, or proline had the least amount of opalescence. It is noted that opalescence in a given formulation does not necessarily correspond to decreased storage stability, such as for F14.

No obvious change in appearance was seen for the stability samples after 1 week of storage at 40° C. or 2 weeks at 25° C. (vs. time-zero). Presence of visible protein particles was not readily apparent in these storage stability samples. However, F3 and F7 showed signs of phase separation after 4 weeks of storage at 5° C. All other samples at 5° C. had equivalent appearance to their time-zero counter-parts.

Viscosity Evaluation

The viscosity evaluation results are presented in Table A2-A3.

TABLE A2

| pH, Concentration and Viscosity (at 25° C.) | | | |
|---|---|---|---|
| Sample | pH | Conc. (mg/mL) | Viscosity (cP) |
| F1 | 4.71 | 149.1 | 19.362 |
| F2 | 4.59 | 151.1 | 12.806 |
| F3 | 4.88 | 151.7 | 15.366 |
| F4 | 4.98 | 149.8 | 17.356 |
| F5 | 5.13 | 151.3 | 14.253 |
| F6 | 4.96 | 151.2 | 14.822 |
| F7 | 4.91 | 146.6 | 11.385 |
| F8 | 5.31 | 151.3 | 18.652 |
| F9 | 5.47 | 150.2 | 11.791 |
| F10 | 5.35 | 151.7 | 8.591 |
| F11 | 5.46 | 149.12 | 15.513 |
| F12 | 5.32 | 152.7 | 15.993 |
| F13 | 5.27 | 149.7 | 35.383 |
| F14 | 5.81 | 153.1 | 8.961 |
| F15 | 5.72 | 152 | 13.882 |
| F16 | 6.31 | 152.96 | 10.58 |
| F17 | 5.2 | 68 | 3.5 |

TABLE A3

| Viscosity (at 25° C.): Listed Lowest to Highest | | | | |
|---|---|---|---|---|
| Sample | pH | Conc. (mg/mL) | Excipients | Viscosity (cP) |
| F10 | 5.35 | 152 | Histidine/Arg * HCl | 8.6 |
| F14 | 5.81 | 153 | Histidine/Arg * Glu | 9.0 |
| F16 | 6.31 | 153 | Histidine/NaCl | 10.6 |
| F7 | 4.91 | 147 | Citrate/NaCl/Arg * HCl | 11.4 |
| F9 | 5.47 | 150 | Histidine/NaCl/Sorbitol | 11.8 |
| F2 | 4.59 | 151 | Succinate/Sorbitol/Arg * HCl | 12.8 |
| F15 | 5.72 | 152 | Citrate/NaCl | 13.9 |
| F5 | 5.13 | 151 | Histidine/NaCl/Proline | 14.3 |
| F6 | 4.96 | 151 | Citrate/Sorbitol/Arg * Glu | 14.8 |
| F3 | 4.88 | 152 | Acetate/NaCl/Arg * HCl | 15.4 |
| F11 | 5.46 | 149 | Histidine/Proline | 15.5 |
| F12 | 5.32 | 153 | Succinate/NaCl | 16.0 |
| F4 | 4.98 | 150 | Succinate/NaCl/Lys * HCl | 17.4 |
| F8 | 5.31 | 151 | Acetate/Sorbitol/Lys * HCl | 18.7 |
| F1 | 4.71 | 149 | Acetate/NaCl | 19.4 |
| F13 | 5.27 | 150 | Acetate/Sucrose | 35.4 |

The data show that inclusion of Arg*HCl, Arg*Glu, and NaCl in a formulation were all effective in lowering viscosity. Histidine was effective in lowering viscosity as well. Use of acetate as a buffer, however, resulted in higher viscosity, and polyols, sucrose, and proline all increased viscosity. The effects of pH on viscosity were not readily apparent.

Size Exclusion Chromatography (SEC): 1 wk 40° C.

SEC was used to measure the loss of monomer and formation of aggregates and/or high molecular weight (HMW) species for the test samples. The results are shown in Table A4-A6.

TABLE A4

| Loss in Monomer Content (% area) for the t1 wk 40° C. Samples vs. Time Zero: Listed Lowest to Highest | | | | |
|---|---|---|---|---|
| Sample | pH | Conc. (mg/mL) | Excipients | Δ % Monomer |
| F17 | 5.17 | 68 | Acetate/Sucrose | −0.19 |
| F14 | 5.81 | 153 | Histidine/Arg * Glu | −0.20 |
| F11 | 5.46 | 149 | Histidine/Proline | −0.27 |
| F9 | 5.47 | 150 | Histidine/NaCl/Sorbitol | −0.34 |
| F8 | 5.31 | 151 | Acetate/Sorbitol/Lys * HCl | −0.39 |
| F16 | 6.31 | 153 | Histidine/NaCl | −0.40 |

TABLE A4-continued

Loss in Monomer Content (% area) for the t1 wk 40° C. Samples vs. Time Zero: Listed Lowest to Highest

| Sample | pH | Conc. (mg/mL) | Excipients | Δ % Monomer |
|---|---|---|---|---|
| F15 | 5.72 | 152 | Citrate/NaCl | −0.41 |
| F10 | 5.35 | 152 | Histidine/Arg * HCl | −0.47 |
| F13 | 5.27 | 150 | Acetate/Sucrose | −0.48 |
| F5 | 5.13 | 151 | Histidine/NaCl/Proline | −0.55 |
| F12 | 5.32 | 153 | Succinate/NaCl | −0.59 |
| F6 | 4.96 | 151 | Citrate/Sorbitol/Arg * Glu | −0.80 |
| F4 | 4.98 | 150 | Succinate/NaCl/Lys * HCl | −1.41 |
| F3 | 4.88 | 152 | Acetate/NaCl/Arg * HCl | −2.40 |
| F7 | 4.91 | 147 | Citrate/NaCl/Arg * HCl | −2.86 |
| F2 | 4.59 | 151 | Succinate/Sorbitol/Arg * HCl | −4.21 |
| F1 | 4.71 | 149 | Acetate/NaCl | −7.44 |

TABLE A5

Increase in Percent Area of the Aggregate (HMW 2) for the t1 wk 40° C. Samples vs. Time-Zero: Listed Lowest to Highest

| Sample | pH | Conc. (mg/mL) | Excipients | Δ % HMW 2 |
|---|---|---|---|---|
| F17 | 5.17 | 68 | Acetate/Sucrose | 0.03 |
| F16 | 6.31 | 153 | Histidine/NaCl | 0.05 |
| F14 | 5.81 | 153 | Histidine/Arg * Glu | 0.05 |
| F11 | 5.46 | 149 | Histidine/Proline | 0.05 |
| F13 | 5.27 | 150 | Acetate/Sucrose | 0.05 |
| F15 | 5.72 | 152 | Citrate/NaCl | 0.05 |
| F9 | 5.47 | 150 | Histidine/NaCl/Sorbitol | 0.08 |
| F8 | 5.31 | 151 | Acetate/Sorbitol/Lys * HCl | 0.09 |
| F12 | 5.32 | 153 | Succinate/NaCl | 0.19 |
| F10 | 5.35 | 152 | Histidine/Arg * HCl | 0.22 |
| F5 | 5.13 | 151 | Histidine/NaCl/Proline | 0.26 |
| F6 | 4.96 | 151 | Citrate/Sorbitol/Arg * Glu | 0.43 |
| F4 | 4.98 | 150 | Succinate/NaCl/Lys * HCl | 1.03 |
| F3 | 4.88 | 152 | Acetate/NaCl/Arg * HCl | 2.08 |
| F7 | 4.91 | 147 | Citrate/NaCl/Arg * HCl | 2.62 |
| F2 | 4.59 | 151 | Succinate/Sorbitol/Arg * HCl | 3.64 |
| F1 | 4.71 | 149 | Acetate/NaCl | 6.97 |

TABLE A6

Increase in HMW 1 (% area) for the t1 wk 40° C. Samples vs. Time Zero: Listed Lowest to Highest

| Sample | pH | Conc. (mg/mL) | Excipients | Δ % HMW 1 |
|---|---|---|---|---|
| F14 | 5.81 | 153 | Histidine/Arg * Glu | 0.14 |
| F17 | 5.17 | 68 | Acetate/Sucrose | 0.18 |
| F10 | 5.35 | 152 | Histidine/Arg * HCl | 0.22 |
| F7 | 4.91 | 147 | Citrate/NaCl/Arg * HCl | 0.23 |
| F11 | 5.46 | 149 | Histidine/Proline | 0.24 |
| F9 | 5.47 | 150 | Histidine/NaCl/Sorbitol | 0.24 |
| F5 | 5.13 | 151 | Histidine/NaCl/Proline | 0.28 |
| F8 | 5.31 | 151 | Acetate/Sorbitol/Lys * HCl | 0.29 |
| F3 | 4.88 | 152 | Acetate/NaCl/Arg * HCl | 0.30 |
| F4 | 4.98 | 150 | Succinate/NaCl/Lys * HCl | 0.34 |
| F16 | 6.31 | 153 | Histidine/NaCl | 0.34 |
| F15 | 5.72 | 152 | Citrate/NaCl | 0.34 |
| F6 | 4.96 | 151 | Citrate/Sorbitol/Arg * Glu | 0.37 |
| F12 | 5.32 | 153 | Succinate/NaCl | 0.38 |
| F1 | 4.71 | 149 | Acetate/NaCl | 0.41 |
| F13 | 5.27 | 150 | Acetate/Sucrose | 0.43 |
| F2 | 4.59 | 151 | Succinate/Sorbitol/Arg * HCl | 0.53 |

Low molecular weight formation was negligible at 1 wk 40° C. Histidine and Arg*Glu were stabilizing under conditions of increasing relative pH. Polyols and proline appeared to be stabilizing as well, or at least were not destabilizing. NaCl was destabilizing under conditions of lower relative pH. However, charged excipients (including NaCl) were less destabilizing under conditions of higher relative pH.

Cation Exchange Chromatography (CEX): Time-Zero and 1 wk 40° C.

CEX was used to measure loss in main peak and changes in acidic or basic peaks after the storage time. The results are presented in Table A7-A10.

TABLE A7

Loss in Main Peak (% area) for the 1 wk 40° C. Samples versus Time-Zero: Listed Lowest to Highest

| Sample | pH | Conc. (mg/mL) | Excipients | Δ % Main Peak |
|---|---|---|---|---|
| F9 | 5.47 | 150 | Histidine/NaCl/Sorbitol | −1.77 |
| F5 | 5.13 | 151 | Histidine/NaCl/Proline | −1.86 |
| F17 | 5.2 | 68 | Acetate/Sucrose | −1.87 |
| F11 | 5.46 | 149 | Histidine/Proline | −1.91 |
| F10 | 5.35 | 152 | Histidine/Arg * HCl | −1.96 |
| F15 | 5.72 | 152 | Citrate/NaCl | −1.98 |
| F8 | 5.31 | 151 | Acetate/Sorbitol/Lys * HCl | −2.04 |
| F13 | 5.27 | 150 | Acetate/Sucrose | −2.07 |
| F12 | 5.32 | 153 | Succinate/NaCl | −2.21 |
| F4 | 4.98 | 150 | Succinate/NaCl/Lys * HCl | −2.57 |
| F14 | 5.81 | 153 | Histidine/Arg * Glu | −2.70 |
| F16 | 6.31 | 153 | Histidine/NaCl | −2.79 |
| F3 | 4.88 | 152 | Acetate/NaCl/Arg * HCl | −2.83 |
| F6 | 4.96 | 151 | Citrate/Sorbitol/Arg * Glu | −4.13 |
| F2 | 4.59 | 151 | Succinate/Sorbitol/Arg * HCl | −5.00 |
| F1 | 4.71 | 149 | Acetate/NaCl | −5.72 |

TABLE A8

Increase in Acidic Peak Region (% area) for the 1 wk 40° C. Samples versus Time-Zero: Listed Lowest to Highest

| Sample | pH | Conc. (mg/mL) | Excipients | Δ % Acidic |
|---|---|---|---|---|
| F1 | 4.71 | 149 | Acetate/NaCl | 0.07 |
| F3 | 4.88 | 152 | Acetate/NaCl/Arg * HCl | 0.37 |
| F5 | 5.13 | 151 | Histidine/NaCl/Proline | 0.78 |
| F9 | 5.47 | 150 | Histidine/NaCl/Sorbitol | 0.82 |
| F4 | 4.98 | 150 | Succinate/NaCl/Lys * HCl | 0.90 |
| F10 | 5.35 | 152 | Histidine/Arg * HCl | 0.96 |
| F11 | 5.46 | 149 | Histidine/Proline | 1.11 |
| F17 | 5.2 | 68 | Acetate/Sucrose | 1.21 |
| F8 | 5.31 | 151 | Acetate/Sorbitol/Lys * HCl | 1.31 |
| F2 | 4.59 | 151 | Succinate/Sorbitol/Arg * HCl | 1.36 |
| F13 | 5.27 | 150 | Acetate/Sucrose | 1.42 |
| F12 | 5.32 | 153 | Succinate/NaCl | 1.56 |
| F15 | 5.72 | 152 | Citrate/NaCl | 1.60 |
| F14 | 5.81 | 153 | Histidine/Arg * Glu | 2.22 |
| F16 | 6.31 | 153 | Histidine/NaCl | 2.77 |
| F6 | 4.96 | 151 | Citrate/Sorbitol/Arg * Glu | 2.85 |

TABLE A9

Increase in Basic Peak Region (% area) for the 1 wk 40° C. Samples versus Time-Zero: Listed Lowest to Highest

| Sample | pH | Conc. (mg/mL) | Excipients | Δ % Basic |
|---|---|---|---|---|
| F16 | 6.31 | 153 | Histidine/NaCl | 0.02 |
| F15 | 5.72 | 152 | Citrate/NaCl | 0.38 |
| F14 | 5.81 | 153 | Histidine/Arg * Glu | 0.48 |
| F12 | 5.32 | 153 | Succinate/NaCl | 0.64 |
| F13 | 5.27 | 150 | Acetate/Sucrose | 0.65 |
| F17 | 5.2 | 68 | Acetate/Sucrose | 0.66 |
| F8 | 5.31 | 151 | Acetate/Sorbitol/Lys * HCl | 0.73 |
| F11 | 5.46 | 149 | Histidine/Proline | 0.80 |

TABLE A9-continued

Increase in Basic Peak Region (% area) for the 1 wk
40° C. Samples versus Time-Zero: Listed Lowest to Highest

| Sample | pH | Conc. (mg/mL) | Excipients | Δ % Basic |
|---|---|---|---|---|
| F9 | 5.47 | 150 | Histidine/NaCl/Sorbitol | 0.96 |
| F10 | 5.35 | 152 | Histidine/Arg * HCl | 0.99 |
| F5 | 5.13 | 151 | Histidine/NaCl/Proline | 1.08 |
| F6 | 4.96 | 151 | Citrate/Sorbitol/Arg * Glu | 1.29 |
| F4 | 4.98 | 150 | Succinate/NaCl/Lys * HCl | 1.67 |
| F3 | 4.88 | 152 | Acetate/NaCl/Arg * HCl | 2.46 |
| F2 | 4.59 | 151 | Succinate/Sorbitol/Arg * HCl | 3.64 |
| F1 | 4.71 | 149 | Acetate/NaCl | 5.65 |

The most chemically stable formulations were those in the pH region of ~5-5.5. A large increase in basic peak content was measured for samples formulated ≤pH 5. This loss was almost entirely to the basic region. Likely, this was aggregated material. At pH values above pH 5.7, main peak loss was generally to the acidic peak region, with the loss presumably due to deamidation.

Size Exclusion Chromatography (SEC): 2 Weeks 25° C.

SEC evaluation results of the samples after 2 weeks at 25° C. are shown in Table A10-A11.

TABLE A10

Loss in Monomer Content (% area) for the t2
wk 25° C. Samples vs. Time Zero: Listed Lowest to Highest

| Sample | pH | Conc. (mg/mL) | Excipients | Δ % Monomer |
|---|---|---|---|---|
| F14 | 5.81 | 153 | Histidine/Arg * Glu | −0.03 |
| F6 | 4.96 | 151 | Citrate/Sorbitol/Arg * Glu | −0.04 |
| F2 | 4.59 | 151 | Succinate/Sorbitol/Arg * HCl | −0.05 |
| F11 | 5.46 | 149 | Histidine/Proline | −0.05 |
| F10 | 5.35 | 152 | Histidine/Arg * HCl | −0.08 |
| F5 | 5.13 | 151 | Histidine/NaCl/Proline | −0.08 |
| F8 | 5.31 | 151 | Acetate/Sorbitol/Lys * HCl | −0.10 |
| F9 | 5.47 | 150 | Histidine/NaCl/Sorbitol | −0.10 |
| F17 | 5.2 | 68 | Acetate/Sucrose | −0.10 |
| F16 | 6.31 | 153 | Histidine/NaCl | −0.12 |
| F3 | 4.88 | 152 | Acetate/NaCl/Arg * HCl | −0.13 |
| F13 | 5.27 | 150 | Acetate/Sucrose | −0.14 |
| F15 | 5.72 | 152 | Citrate/NaCl | −0.18 |
| F12 | 5.32 | 153 | Succinate/NaCl | −0.19 |
| F7 | 4.91 | 147 | Citrate/NaCl/Arg * HCl | −0.19 |
| F1 | 4.71 | 149 | Acetate/NaCl | −0.20 |
| F4 | 4.98 | 150 | Succinate/NaCl/Lys * HCl | −0.23 |

TABLE A11

Increase in HMW 1 (% area) for the t2 wk 25° C.
Samples vs. Time Zero: Listed Lowest to Highest

| Sample | pH | Conc. (mg/mL) | Excipients | Δ % HMW 1 |
|---|---|---|---|---|
| F14 | 5.81 | 153 | Histidine/Arg * Glu | 0.02 |
| F6 | 4.96 | 151 | Citrate/Sorbitol/Arg * Glu | 0.04 |
| F10 | 5.35 | 152 | Histidine/Arg * HCl | 0.05 |
| F5 | 5.13 | 151 | Histidine/NaCl/Proline | 0.06 |
| F11 | 5.46 | 149 | Histidine/Proline | 0.06 |
| F9 | 5.47 | 150 | Histidine/NaCl/Sorbitol | 0.07 |
| F2 | 4.59 | 151 | Succinate/Sorbitol/Arg * HCl | 0.07 |
| F8 | 5.31 | 151 | Acetate/Sorbitol/Lys * HCl | 0.09 |
| F17 | 5.2 | 68 | Acetate/Sucrose | 0.10 |
| F3 | 4.88 | 152 | Acetate/NaCl/Arg * HCl | 0.11 |
| F16 | 6.31 | 153 | Histidine/NaCl | 0.13 |
| F1 | 4.71 | 149 | Acetate/NaCl | 0.14 |
| F12 | 5.32 | 153 | Succinate/NaCl | 0.16 |
| F13 | 5.27 | 150 | Acetate/Sucrose | 0.17 |
| F7 | 4.91 | 147 | Citrate/NaCl/Arg * HCl | 0.17 |
| F15 | 5.72 | 152 | Citrate/NaCl | 0.17 |
| F4 | 4.98 | 150 | Succinate/NaCl/Lys * HCl | 0.19 |

Low molecular weight formation was negligible at 2 wks 25° C. Additionally, formation of HMW 2 (aggregate) was negligible at 2 wks 25° C. This suggests that the 40° C. condition is not necessarily predictive of HMW formation at lower temperatures. Histidine and Arg*Glu appeared to be the most stabilizing excipients. Arg*HCl, sorbitol, and proline appeared to be stabilizing as well, or at least were not destabilizing.

Multiple formulations had equivalent stability as the stock solution/drug substance (F17) at 2 weeks 25° C. The lowest viscosity formulations (F10 and F14) were among those having equivalent stability. F14 was the best performing formulation, consistent with the last result.

Cation Exchange Chromatography (CEX): 2 Weeks 25° C.

The CEX results for 2 weeks at 25° C. are shown in Tables A12-A14.

TABLE A12

Loss in Main Peak (% area) for the 2 wk
25° C. Samples versus Time-Zero: Listed Lowest to Highest

| Sample | pH | Conc. (mg/mL) | Excipients | Δ % Main Peak |
|---|---|---|---|---|
| F13 | 5.27 | 150 | Acetate/Sucrose | −0.26 |
| F9 | 5.47 | 150 | Histidine/NaCl/Sorbitol | −0.33 |
| F5 | 5.13 | 151 | Histidine/NaCl/Proline | −0.40 |
| F4 | 4.98 | 150 | Succinate/NaCl/Lys * HCl | −0.42 |
| F11 | 5.46 | 149 | Histidine/Proline | −0.43 |
| F14 | 5.81 | 153 | Histidine/Arg * Glu | −0.45 |
| F17 | 5.2 | 68 | Acetate/Sucrose | −0.54 |
| F12 | 5.32 | 153 | Succinate/NaCl | −0.58 |
| F10 | 5.35 | 152 | Histidine/Arg * HCl | −0.64 |
| F16 | 6.31 | 153 | Histidine/NaCl | −0.65 |
| F8 | 5.31 | 151 | Acetate/Sorbitol/Lys * HCl | −0.66 |
| F15 | 5.72 | 152 | Citrate/NaCl | −0.71 |
| F3 | 4.88 | 152 | Acetate/NaCl/Arg * HCl | −0.83 |
| F2 | 4.59 | 151 | Succinate/Sorbitol/Arg * HCl | −0.84 |
| F1 | 4.71 | 149 | Acetate/NaCl | −0.87 |
| F6 | 4.96 | 151 | Citrate/Sorbitol/Arg * Glu | −1.25 |

TABLE A13

Change in Acidic Peak Region (% area) for the 2 wk
25° C. Samples versus Time-Zero: Listed Lowest to Highest

| Sample | pH | Conc. (mg/mL) | Excipients | Δ % Acidic |
|---|---|---|---|---|
| F4 | 4.98 | 150 | Succinate/NaCl/Lys * HCl | −0.23 |
| F9 | 5.47 | 150 | Histidine/NaCl/Sorbitol | −0.16 |
| F5 | 5.13 | 151 | Histidine/NaCl/Proline | 0.03 |
| F13 | 5.27 | 150 | Acetate/Sucrose | 0.08 |
| F14 | 5.81 | 153 | Histidine/Arg * Glu | 0.08 |
| F11 | 5.46 | 149 | Histidine/Proline | 0.09 |
| F12 | 5.32 | 153 | Succinate/NaCl | 0.13 |
| F8 | 5.31 | 151 | Acetate/Sorbitol/Lys * HCl | 0.15 |
| F10 | 5.35 | 152 | Histidine/Arg * HCl | 0.15 |
| F2 | 4.59 | 151 | Succinate/Sorbitol/Arg * HCl | 0.21 |
| F3 | 4.88 | 152 | Acetate/NaCl/Arg * HCl | 0.24 |
| F1 | 4.71 | 149 | Acetate/NaCl | 0.26 |

TABLE A13-continued

Change in Acidic Peak Region (% area) for the 2 wk
25° C. Samples versus Time-Zero: Listed Lowest to Highest

| Sample | pH | Conc. (mg/mL) | Excipients | Δ % Acidic |
|---|---|---|---|---|
| F17 | 5.2 | 68 | Acetate/Sucrose | 0.27 |
| F15 | 5.72 | 152 | Citrate/NaCl | 0.46 |
| F16 | 6.31 | 153 | Histidine/NaCl | 0.55 |
| F6 | 4.96 | 151 | Citrate/Sorbitol/Arg * Glu | 0.79 |

TABLE A14

Increase in Basic Peak Region (% area) for the 2 wk
25° C. Samples versus Time-Zero: Listed Lowest to Highest

| Sample | pH | Conc. (mg/mL) | Excipients | Δ % Basic |
|---|---|---|---|---|
| F16 | 6.31 | 153 | Histidine/NaCl | 0.10 |
| F13 | 5.27 | 150 | Acetate/Sucrose | 0.18 |
| F15 | 5.72 | 152 | Citrate/NaCl | 0.25 |
| F17 | 5.2 | 68 | Acetate/Sucrose | 0.27 |
| F11 | 5.46 | 149 | Histidine/Proline | 0.33 |
| F5 | 5.13 | 151 | Histidine/NaCl/Proline | 0.36 |
| F14 | 5.81 | 153 | Histidine/Arg * Glu | 0.37 |
| F12 | 5.32 | 153 | Succinate/NaCl | 0.45 |
| F6 | 4.96 | 151 | Citrate/Sorbitol/Arg * Glu | 0.46 |
| F10 | 5.35 | 152 | Histidine/Arg * HCl | 0.49 |
| F9 | 5.47 | 150 | Histidine/NaCl/Sorbitol | 0.49 |
| F8 | 5.31 | 151 | Acetate/Sorbitol/Lys * HCl | 0.51 |
| F3 | 4.88 | 152 | Acetate/NaCl/Arg * HCl | 0.60 |
| F1 | 4.71 | 149 | Acetate/NaCl | 0.61 |
| F2 | 4.59 | 151 | Succinate/Sorbitol/Arg * HCl | 0.63 |
| F4 | 4.98 | 150 | Succinate/NaCl/Lys * HCl | 0.65 |

Trends at 25° C. were similar to those seen at 40° C., although the rates of degradation were much lower. Differences for some formulations were within the error of the assay (±0.3% area for the main-peak). The most chemically stable formulations were those in the pH region of ~5.1-5.8. Basic peak content generally increased as a function of decreasing pH, and was most pronounced for samples formulated ≤pH 5. Above pH 5.7, main peak loss was generally to the acidic peak region. Presumably, this loss was due to deamidation. Citrate appears to be destabilizing, whereas the effects of other excipients are harder to discern.

Size Exclusion Chromatography (SEC): 4 Weeks 2-8° C.

SEC evaluation of the samples after 4 weeks at 2-8° C. was also performed. Most changes at 4 wks 2-8° C. were within the error of the assay, i.e., no measurable degradation. However, F03 and F07 had experienced phase separation. Low pH (relative), salt, and citrate are thought to be primary factors causing this phase separation. Phase separation only occurred at the 2-8° C. storage temperature.

Cation Exchange Chromatography (CEX): 4 Weeks 2-8° C.

The CEX results for 4 weeks at 2-8° C. are shown in Tables A15-A16.

TABLE A15

Loss in Main Peak (% area) for the 4 wk 2-8° C.
Samples versus Time-Zero: Listed Lowest to Highest

| Sample | pH | Conc. (mg/mL) | Excipients | Δ % Main Peak |
|---|---|---|---|---|
| F16 | 6.31 | 153 | Histidine/NaCl | 0.02 |
| F14 | 5.81 | 153 | Histidine/Arg * Glu | 0.01 |
| F13 | 5.27 | 150 | Acetate/Sucrose | 0.00 |
| F9 | 5.47 | 150 | Histidine/NaCl/Sorbitol | −0.08 |
| F12 | 5.32 | 153 | Succinate/NaCl | −0.08 |
| F11 | 5.46 | 149 | Histidine/Proline | −0.15 |
| F4 | 4.98 | 150 | Succinate/NaCl/Lys * HCl | −0.19 |
| F8 | 5.31 | 151 | Acetate/Sorbitol/Lys * HCl | −0.19 |
| F5 | 5.13 | 151 | Histidine/NaCl/Proline | −0.24 |
| F17 | 5.2 | 68 | Acetate/Sucrose | −0.25 |
| F15 | 5.72 | 152 | Citrate/NaCl | −0.48 |
| F1 | 4.71 | 149 | Acetate/NaCl | −0.50 |
| F2 | 4.59 | 151 | Succinate/Sorbitol/Arg * HCl | −0.56 |
| F10 | 5.35 | 152 | Histidine/Arg * HCl | −0.62 |
| F6 | 4.96 | 151 | Citrate/Sorbitol/Arg * Glu | −0.69 |

TABLE A16

Increase in Basic Peak Region (% area) for the 4 wk
2-8° C. Samples versus Time-Zero: Listed Lowest to Highest

| Sample | pH | Conc. (mg/mL) | Excipients | Δ % Basic |
|---|---|---|---|---|
| F17 | 5.2 | 68 | Acetate/Sucrose | 0.03 |
| F13 | 5.27 | 150 | Acetate/Sucrose | 0.14 |
| F8 | 5.31 | 151 | Acetate/Sorbitol/Lys * HCl | 0.22 |
| F14 | 5.81 | 153 | Histidine/Arg * Glu | 0.25 |
| F16 | 6.31 | 153 | Histidine/NaCl | 0.25 |
| F4 | 4.98 | 150 | Succinate/NaCl/Lys * HCl | 0.29 |
| F12 | 5.32 | 153 | Succinate/NaCl | 0.31 |
| F5 | 5.13 | 151 | Histidine/NaCl/Proline | 0.43 |
| F11 | 5.46 | 149 | Histidine/Proline | 0.44 |
| F6 | 4.96 | 151 | Citrate/Sorbitol/Arg * Glu | 0.45 |
| F2 | 4.59 | 151 | Succinate/Sorbitol/Arg * HCl | 0.52 |
| F15 | 5.72 | 152 | Citrate/NaCl | 0.56 |
| F9 | 5.47 | 150 | Histidine/NaCl/Sorbitol | 0.58 |
| F1 | 4.71 | 149 | Acetate/NaCl | 0.60 |
| F10 | 5.35 | 152 | Histidine/Arg * HCl | 0.64 |

Differences in main-peak (% area) for most formulations were within the error of the assay (±0.3% area for the main-peak). Change in acidic peak content was generally not significant.

Overall, the experiments of Example 3 demonstrate that histidine was the best performing buffer species, as it stabilized the samples under accelerated and stressed temperature conditions and led to lower viscosity.

Arg*Glu and Arg*HCl were the most impactful excipients for reducing viscosity. Arg*Glu had the better stability profile, although the differences were generally small. Arg*Glu, Arg*HCl, sucrose, sorbitol, and proline were generally stabilizing, but the latter 3 increased viscosity. NaCl and citrate were destabilizing, especially at pH values ≤5. They tended to cause phase separation at 2-8° C. storage. Arginine may be de-stabilizing at lower relative pH as well.

From this data set, chemical stability appears to be optimal at pH ≥5.1 and pH ≤5.8. AM001 was physically stable in this pH range as well. The stability was excipient-dependent. Among all samples, F14 (pH 5.8) had the overall best properties.

Example 4. Refinement of Formulation Conditions

Example 3 demonstrated that AM001 formulated with histidine and an arginine salt (HCl or glutamate) had the lowest viscosities and favorable stability profiles. This example then investigated the stability of AM001 as a function of buffer type (succinate or histidine), pH, and arginine salt type (HCl, Glutamate, or Aspartate) in greater detail. In addition, the stability of sugar/polyol formulations containing an arginine salt were examined.

The pH range tested here was from 5.2 to 5.8. The experimental design is similar to Example 3. The tested samples are shown in Table B1.

TABLE B1

Listing of Tested Formulation Samples (F1-F15)

| Sample | Protein (mg/mL) | pH | Acetate (mM) | Succinate (mM) | Histidine (mM) | Arg * HCl (mM) | Arg * Glu (mM) | Arg * Asp (mM) | Sucrose (mM) | Sorbitol (mM) | % PS20 (w/v) |
|---|---|---|---|---|---|---|---|---|---|---|---|
| F1  | 150 | 5.2 |    | 20 |    |     | 150 |     |     |     | 0.009 |
| F2  | 150 | 5.2 |    |    | 20 | 75  |     |     | 135 |     | 0.009 |
| F3  | 150 | 5.2 |    |    | 20 |     | 75  |     |     | 135 | 0.009 |
| F4  | 150 | 5.2 |    |    | 20 | 150 |     |     |     |     | 0.009 |
| F5  | 150 | 5.2 |    |    | 20 |     | 150 |     |     |     | 0.009 |
| F6  | 150 | 5.2 |    |    | 20 |     |     | 150 |     |     | 0.009 |
| F7  | 150 | 5.5 |    |    | 20 | 150 |     |     |     |     | 0.009 |
| F8  | 150 | 5.5 |    | 20 |    | 150 |     |     |     |     | 0.009 |
| F9  | 150 | 5.5 |    |    | 20 |     | 150 |     |     |     | 0.009 |
| F10 | 150 | 5.5 |    |    | 40 |     | 150 |     |     |     | 0.009 |
| F11 | 150 | 5.5 |    |    | 20 |     |     | 150 |     |     | 0.009 |
| F12 | 150 | 5.8 |    |    | 20 |     | 150 |     |     |     | 0.009 |
| F13 | 150 | 5.8 |    |    | 20 | 120 |     |     |     | 60  | 0.009 |
| F14 | 150 | 5.8 |    |    | 20 |     | 120 |     | 60  |     | 0.009 |
| F15 | 70  | 5.2 | 10 |    |    |     |     |     | 260 |     | 0.004 |

*F15 is the stock solution

Visual Observations

No obvious change in the appearance of stability samples was observed after 1 week of storage at 40° C. (vs. time-zero). This was true for the other time-points in this study as well. Presence of visible protein particles was not readily apparent in any storage stability samples.

Viscosity Evaluation

The viscosity evaluation results are presented in Table B2.

TABLE B2

Viscosity (at 25° C.): Listed Lowest to Highest

| Sample | pH | Conc. (mg/mL) | Excipients | Viscosity (mPa * s) |
|---|---|---|---|---|
| F7  | 5.51 | 149 | His/Arg * HCl | 7.0 |
| F13 | 5.79 | 152 | His/120 mM Arg * HCl/Sorbitol | 7.6 |
| F10 | 5.53 | 149 | 40 mM His/Arg * Glu | 7.7 |
| F12 | 5.77 | 151 | His/Arg * Glu | 7.8 |
| F8  | 5.46 | 150 | Succ/Arg * HCl | 7.8 |
| F11 | 5.57 | 150 | His/Arg * Asp | 7.9 |
| F9  | 5.52 | 152 | His/Arg * Glu | 8.2 |
| F4  | 5.24 | 151 | His/Arg * HCl | 8.3 |
| F5  | 5.18 | 151 | His/Arg * Glu | 8.6 |
| F6  | 5.2  | 152 | His/Arg * Asp | 8.8 |
| F14 | 5.79 | 154 | His/120 mM Arg * Glu/Sucrose | 8.8 |
| F1  | 5.14 | 151 | Succ/Arg * Glu | 8.9 |
| F2  | 5.29 | 150 | His/75 mM Arg * HCl/Sucrose | 9.8 |
| F3  | 5.22 | 151 | His/75 mM Arg * Glu/Sorbitol | 10.1 |

As shown in the data, viscosity was below 10 mPa*s for most formulations. Arg*HCl, however, lowered viscosity slightly more than Arg*Glu or Arg*Asp. Sugars and polyols, by contrast, increased the viscosity of the solution when co-formulated with the arginine salt. Also, increasing the histidine concentration (from 20 to 40 mM) had a minimal impact on lowering viscosity. In terms of the impact of pH, viscosity was generally higher for all formulations at pH 5.2 versus those at pH 5.5 and above Size Exclusion Chromatography (SEC): 1 wk 40° C.

SEC was used to measure the loss of monomer and formation of aggregates and/or high molecular weight (HMW) species for the test samples. The results are shown in Table B3-B5.

TABLE B3

Loss in Monomer Content (% area) for the t1 wk 40° C. Samples vs. Time Zero: Listed Lowest to Highest

| Sample | pH | Conc. (mg/mL) | Excipients | Δ % Monomer |
|---|---|---|---|---|
| F12 | 5.77 | 151 | His/Arg * Glu | −0.12 |
| F9  | 5.52 | 152 | His/Arg * Glu | −0.14 |
| F14 | 5.79 | 154 | His/120 mM Arg * Glu/Sucrose | −0.17 |
| F15 | 5.2  | 68  | Acetate/Sucrose (Ctrl) | −0.18 |
| F13 | 5.79 | 152 | His/120 mM Arg * HCl/Sorbitol | −0.20 |
| F11 | 5.57 | 150 | His/Arg * Asp | −0.21 |
| F10 | 5.53 | 149 | 40 mM His/Arg * Glu | −0.22 |
| F3  | 5.22 | 151 | His/75 mM Arg * Glu/Sorbitol | −0.25 |
| F5  | 5.18 | 151 | His/Arg * Glu | −0.29 |
| F2  | 5.29 | 150 | His/75 mM Arg * HCl/Sucrose | −0.30 |
| F6  | 5.2  | 152 | His/Arg * Asp | −0.31 |
| F7  | 5.51 | 149 | His/Arg * HCl | −0.31 |
| F8  | 5.46 | 150 | Succ/Arg * HCl | −0.31 |
| F1  | 5.14 | 151 | Succ/Arg * Glu | −0.33 |
| F4  | 5.24 | 151 | His/Arg * HCl | −0.46 |

TABLE B4

Increase in Percent Area of the Aggregate (HMW 2) for the t1 wk 40° C. Samples vs. Time Zero: Listed Lowest to Highest

| Sample | pH | Conc. (mg/mL) | Excipients | Δ % HMW 2 |
|---|---|---|---|---|
| F12 | 5.77 | 151 | His/Arg * Glu | 0.01 |
| F15 | 5.2  | 68  | Acetate/Sucrose (Ctrl) | 0.01 |
| F14 | 5.79 | 154 | His/120 mM Arg * Glu/Sucrose | 0.04 |
| F9  | 5.52 | 152 | His/Arg * Glu | 0.05 |
| F13 | 5.79 | 152 | His/120 mM Arg * HCl/Sorbitol | 0.05 |
| F11 | 5.57 | 150 | His/Arg * Asp | 0.07 |
| F10 | 5.53 | 149 | 40 mM His/Arg * Glu | 0.07 |
| F3  | 5.22 | 151 | His/75 mM Arg * Glu/Sorbitol | 0.09 |
| F8  | 5.46 | 150 | Succ/Arg * HCl | 0.11 |
| F2  | 5.29 | 150 | His/75 mM Arg * HCl/Sucrose | 0.12 |
| F1  | 5.14 | 151 | Succ/Arg * Glu | 0.12 |
| F6  | 5.2  | 152 | His/Arg * Asp | 0.13 |
| F7  | 5.51 | 149 | His/Arg * HCl | 0.14 |
| F5  | 5.18 | 151 | His/Arg * Glu | 0.14 |
| F4  | 5.24 | 151 | His/Arg * HCl | 0.27 |

TABLE B5

Increase in HMW 1 (% area) for the t1 wk 40° C.
Samples vs. Time Zero: Listed Lowest to Highest

| Sample | pH | Conc. (mg/mL) | Excipients | Δ % HMW 1 |
|---|---|---|---|---|
| F9 | 5.52 | 152 | His/Arg * Glu | 0.10 |
| F12 | 5.77 | 151 | His/Arg * Glu | 0.10 |
| F14 | 5.79 | 154 | His/120 mM Arg * Glu/Sucrose | 0.12 |
| F13 | 5.79 | 152 | His/120 mM Arg * HCl/Sorbitol | 0.13 |
| F10 | 5.53 | 149 | 40 mM His/Arg * Glu | 0.13 |
| F11 | 5.57 | 150 | His/Arg * Asp | 0.13 |
| F5 | 5.18 | 151 | His/Arg * Glu | 0.14 |
| F3 | 5.22 | 151 | His/75 mM Arg * Glu/Sorbitol | 0.15 |
| F7 | 5.51 | 149 | His/Arg * HCl | 0.15 |
| F15 | 5.2 | 68 | Acetate/Sucrose (Ctrl) | 0.16 |
| F2 | 5.29 | 150 | His/75 mM Arg * HCl/Sucrose | 0.16 |
| F6 | 5.2 | 152 | His/Arg * Asp | 0.16 |
| F8 | 5.46 | 150 | Succ/Arg * HCl | 0.18 |
| F4 | 5.24 | 151 | His/Arg * HCl | 0.18 |
| F1 | 5.14 | 151 | Succ/Arg * Glu | 0.19 |

The trends here were consistent with those observed in Example 3. Low molecular weight formation was negligible at 1 wk 40° C. Arg*Glu was generally more stabilizing than Arg*HCl at equivalent pH. Arg*Asp performed similarly to Arg*Glu. Loss of main peak was generally minimized above pH 5.5.

No improvement in stability was observed by formulating the arginine salts with a sugar or polyol. Succinate buffer provided no improvement in stability versus histidine buffer. Cation Exchange Chromatography (CEX): Time-Zero and 1 wk 40° C.

The CEX results for 1 week at 40° C. are shown in Tables B6-B8.

TABLE B6

Loss in Main Peak (% area) for the 1 wk 40° C.
Samples versus Time-Zero: Listed Lowest to Highest

| Sample | pH | Conc. (mg/mL) | Excipients | Δ % Main Peak |
|---|---|---|---|---|
| F12 | 5.77 | 151 | His/Arg * Glu | −1.15 |
| F9 | 5.52 | 152 | His/Arg * Glu | −1.38 |
| F4 | 5.24 | 151 | His/Arg * HCl | −1.44 |
| F7 | 5.51 | 149 | His/Arg * HCl | −1.47 |
| F11 | 5.57 | 150 | His/Arg * Asp | −1.50 |
| F8 | 5.46 | 150 | Succ/Arg * HCl | −1.51 |
| F10 | 5.53 | 149 | 40 mM His/Arg * Glu | −1.52 |
| F13 | 5.79 | 152 | His/120 mM Arg * HCl/Sorbitol | −1.55 |
| F3 | 5.22 | 151 | His/75 mM Arg * Glu/Sorbitol | −1.68 |
| F5 | 5.18 | 151 | His/Arg * Glu | −1.71 |
| F1 | 5.14 | 151 | Succ/Arg * Glu | −1.75 |
| F14 | 5.79 | 154 | His/120 mM Arg * Glu/Sucrose | −1.78 |
| F15 | 5.2 | 68 | Acetate/Sucrose (Ctrl) | −1.87 |
| F2 | 5.29 | 150 | His/75 mM Arg * HCl/Sucrose | −1.87 |
| F6 | 5.2 | 152 | His/Arg * Asp | −2.02 |

TABLE B7

Increase in Acidic Peak Region (% area) for the
1 wk 40° C. Samples versus Time-Zero: Listed Lowest to Highest

| Sample | pH | Conc. (mg/mL) | Excipients | Δ % Acidic |
|---|---|---|---|---|
| F7 | 5.51 | 149 | His/Arg * HCl | 0.56 |
| F1 | 5.14 | 151 | Succ/Arg * Glu | 0.76 |
| F4 | 5.24 | 151 | His/Arg * HCl | 0.76 |
| F5 | 5.18 | 151 | His/Arg * Glu | 0.81 |
| F3 | 5.22 | 151 | His/75 mM Arg * Glu/Sorbitol | 0.90 |
| F6 | 5.2 | 152 | His/Arg * Asp | 0.92 |
| F12 | 5.77 | 151 | His/Arg * Glu | 0.94 |
| F2 | 5.29 | 150 | His/75 mM Arg * HCl/Sucrose | 0.97 |
| F8 | 5.46 | 150 | Succ/Arg * HCl | 1.00 |
| F13 | 5.79 | 152 | His/120 mM Arg * HCl/Sorbitol | 1.03 |
| F11 | 5.57 | 150 | His/Arg * Asp | 1.04 |
| F9 | 5.52 | 152 | His/Arg * Glu | 1.04 |
| F15 | 5.2 | 68 | Acetate/Sucrose (Ctrl) | 1.10 |
| F10 | 5.53 | 149 | 40 mM His/Arg * Glu | 1.11 |
| F14 | 5.79 | 154 | His/120 mM Arg * Glu/Sucrose | 1.48 |

TABLE B8

Increase in Basic Peak Region (% area) for the 1 wk
40° C. Samples versus Time-Zero: Listed Lowest to Highest

| Sample | pH | Conc. (mg/mL) | Excipients | Δ % Basic |
|---|---|---|---|---|
| F12 | 5.77 | 151 | His/Arg * Glu | 0.22 |
| F14 | 5.79 | 154 | His/120 mM Arg * Glu/Sucrose | 0.30 |
| F9 | 5.52 | 152 | His/Arg * Glu | 0.35 |
| F10 | 5.53 | 149 | 40 mM His/Arg * Glu | 0.40 |
| F11 | 5.57 | 150 | His/Arg * Asp | 0.46 |
| F8 | 5.46 | 150 | Succ/Arg * HCl | 0.50 |
| F13 | 5.79 | 152 | His/120 mM Arg * HCl/Sorbitol | 0.52 |
| F4 | 5.24 | 151 | His/Arg * HCl | 0.68 |
| F15 | 5.2 | 68 | Acetate/Sucrose (Ctrl) | 0.77 |
| F3 | 5.22 | 151 | His/75 mM Arg * Glu/Sorbitol | 0.78 |
| F5 | 5.18 | 151 | His/Arg * Glu | 0.90 |
| F7 | 5.51 | 149 | His/Arg * HCl | 0.90 |
| F2 | 5.29 | 150 | His/75 mM Arg * HCl/Sucrose | 0.90 |
| F1 | 5.14 | 151 | Succ/Arg * Glu | 0.99 |
| F6 | 5.2 | 152 | His/Arg * Asp | 1.09 |

These results show that loss of main peak was minimized at pH >5.2, and was largely equivalent for all three arginine salts in the pH range of 5.5-5.8. There was no obvious advantage to formulate with a sugar or polyol versus the arginine salt alone. Additionally, succinate buffer provided no improvement in chemical stability versus histidine buffer. Multiple formulations had equivalent chemical stability as the stock solution/drug substance (F15).

The analyses were repeated after 2 weeks storage at 25° C. The results are shown in Table B9-B11.

TABLE B9

Loss in Main Peak (% area) for the 2 wk 25° C.
Samples versus Time-Zero: Listed Lowest to Highest

| Sample | pH | Conc. (mg/mL) | Excipients | Δ % Main Peak |
|---|---|---|---|---|
| F12 | 5.77 | 151 | His/Arg * Glu | −0.17 |
| F11 | 5.57 | 150 | His/Arg * Asp | −0.23 |
| F4 | 5.24 | 151 | His/Arg * HCl | −0.34 |
| F13 | 5.79 | 152 | His/120 mM Arg * HCl/Sorbitol | −0.36 |
| F14 | 5.79 | 154 | His/120 mM Arg * Glu/Sucrose | −0.51 |
| F3 | 5.22 | 151 | His/75 mM Arg * Glu/Sorbitol | −0.60 |
| F5 | 5.18 | 151 | His/Arg * Glu | −0.61 |
| F6 | 5.2 | 152 | His/Arg * Asp | −0.65 |
| F8 | 5.46 | 150 | Succ/Arg * HCl | −0.66 |
| F15 | 5.2 | 68 | Acetate/Sucrose (Ctrl) | −0.67 |
| F9 | 5.52 | 152 | His/Arg * Glu | −0.75 |
| F10 | 5.53 | 149 | 40 mM His/Arg * Glu | −0.79 |

TABLE B9-continued

Loss in Main Peak (% area) for the 2 wk 25° C. Samples versus Time-Zero: Listed Lowest to Highest

| Sample | pH | Conc. (mg/mL) | Excipients | Δ % Main Peak |
|---|---|---|---|---|
| F7 | 5.51 | 149 | His/Arg * HCl | −0.82 |
| F2 | 5.29 | 150 | His/75 mM Arg * HCl/Sucrose | −1.02 |
| F1 | 5.14 | 151 | Succ/Arg * Glu | −1.10 |

TABLE B10

Increase in Acidic Peak Region (% area) for the 2 wk 25° C. Samples versus Time-Zero: Listed Lowest to Highest

| Sample | pH | Conc. (mg/mL) | Excipients | Δ % Acidic |
|---|---|---|---|---|
| F13 | 5.79 | 152 | His/120 mM Arg * HCl/Sorbitol | 0.16 |
| F3 | 5.22 | 151 | His/75 mM Arg * Glu/Sorbitol | 0.17 |
| F15 | 5.2 | 68 | Acetate/Sucrose (Ctrl) | 0.18 |
| F8 | 5.46 | 150 | Succ/Arg * HCl | 0.21 |
| F7 | 5.51 | 149 | His/Arg * HCl | 0.21 |
| F11 | 5.57 | 150 | His/Arg * Asp | 0.23 |
| F14 | 5.79 | 154 | His/120 mM Arg * Glu/Sucrose | 0.23 |
| F12 | 5.77 | 151 | His/Arg * Glu | 0.26 |
| F4 | 5.24 | 151 | His/Arg * HCl | 0.27 |
| F6 | 5.2 | 152 | His/Arg * Asp | 0.29 |
| F9 | 5.52 | 152 | His/Arg * Glu | 0.35 |
| F5 | 5.18 | 151 | His/Arg * Glu | 0.36 |
| F1 | 5.14 | 151 | Succ/Arg * Glu | 0.38 |
| F10 | 5.53 | 149 | 40 mM His/Arg * Glu | 0.40 |
| F2 | 5.29 | 150 | His/75 mM Arg * HCl/Sucrose | 0.49 |

TABLE B11

Change in Basic Peak Region (% area) for the 2 wk 25° C. Samples versus Time-Zero: Listed Lowest to Highest

| Sample | pH | Conc. (mg/mL) | Excipients | Δ % Basic |
|---|---|---|---|---|
| F12 | 5.77 | 151 | His/Arg * Glu | −0.09 |
| F11 | 5.57 | 150 | His/Arg * Asp | 0.00 |
| F4 | 5.24 | 151 | His/Arg * HCl | 0.07 |
| F13 | 5.79 | 152 | His/120 mM Arg * HCl/Sorbitol | 0.20 |
| F5 | 5.18 | 151 | His/Arg * Glu | 0.25 |
| F14 | 5.79 | 154 | His/120 mM Arg * Glu/Sucrose | 0.28 |
| F6 | 5.2 | 152 | His/Arg * Asp | 0.35 |
| F10 | 5.53 | 149 | 40 mM His/Arg * Glu | 0.39 |
| F9 | 5.52 | 152 | His/Arg * Glu | 0.39 |
| F3 | 5.22 | 151 | His/75 mM Arg * Glu/Sorbitol | 0.43 |
| F8 | 5.46 | 150 | Succ/Arg * HCl | 0.46 |
| F15 | 5.2 | 68 | Acetate/Sucrose (Ctrl) | 0.48 |
| F2 | 5.29 | 150 | His/75 mM Arg * HCl/Sucrose | 0.53 |
| F7 | 5.51 | 149 | His/Arg * HCl | 0.60 |
| F1 | 5.14 | 151 | Succ/Arg * Glu | 0.72 |

Loss of main peak was minimal for the majority of samples after 2 weeks of storage at 25° C. Generally, loss appeared to be least for those samples formulated at pH 5.8. Again, there was no obvious advantage to formulating with a sugar or polyol versus the arginine salt alone. Succinate buffer provided no improvement in chemical stability versus histidine buffer. Moreover, multiple formulations had equivalent chemical stability as the stock solution/drug substance (F15).

The analyses were also conducted after 5 weeks storage at 2-8° C. The results are shown in Table B12-B14.

TABLE B12

Change in Main Peak (% area) for the 5 wk 2-8° C. Samples versus Time-Zero

| Sample | pH | Conc. (mg/mL) | Excipients | Δ % Main Peak |
|---|---|---|---|---|
| F1 | 5.14 | 151 | Succ/Arg * Glu | 0.13 |
| F2 | 5.29 | 150 | His/75 mM Arg * HCl/Sucrose | −0.59 |
| F3 | 5.22 | 151 | His/75 mM Arg * Glu/Sorbitol | −0.23 |
| F4 | 5.24 | 151 | His/Arg * HCl | −0.05 |
| F5 | 5.18 | 151 | His/Arg * Glu | −0.40 |
| F6 | 5.2 | 152 | His/Arg * Asp | −0.38 |
| F7 | 5.51 | 149 | His/Arg * HCl | −0.37 |
| F8 | 5.46 | 150 | Succ/Arg * HCl | −0.13 |
| F9 | 5.52 | 152 | His/Arg * Glu | −0.22 |
| F10 | 5.53 | 149 | 40 mM His/Arg * Glu | −0.06 |
| F11 | 5.57 | 150 | His/Arg * Asp | 0.15 |
| F12 | 5.77 | 151 | His/Arg * Glu | −0.19 |
| F13 | 5.79 | 152 | His/120 mM Arg * HCl/Sorbitol | 0.01 |
| F14 | 5.79 | 154 | His/120 mM Arg * Glu/Sucrose | −0.03 |
| F15 | 5.2 | 68 | Acetate/Sucrose (Ctrl) | −0.57 |

TABLE B13

Change in Acidic Peak Region (% area) for the 5 wk 2-8° C. Samples versus Time-Zero

| Sample | pH | Conc. (mg/mL) | Excipients | Δ % Acidic |
|---|---|---|---|---|
| F1 | 5.14 | 151 | Succ/Arg * Glu | −0.45 |
| F2 | 5.29 | 150 | His/75 mM Arg * HCl/Sucrose | 0.19 |
| F3 | 5.22 | 151 | His/75 mM Arg * Glu/Sorbitol | −0.10 |
| F4 | 5.24 | 151 | His/Arg * HCl | −0.22 |
| F5 | 5.18 | 151 | His/Arg * Glu | −0.04 |
| F6 | 5.2 | 152 | His/Arg * Asp | 0.03 |
| F7 | 5.51 | 149 | His/Arg * HCl | −0.07 |
| F8 | 5.46 | 150 | Succ/Arg * HCl | −0.19 |
| F9 | 5.52 | 152 | His/Arg * Glu | 0.07 |
| F10 | 5.53 | 149 | 40 mM His/Arg * Glu | 0.02 |
| F11 | 5.57 | 150 | His/Arg * Asp | −0.09 |
| F12 | 5.77 | 151 | His/Arg * Glu | 0.05 |
| F13 | 5.79 | 152 | His/120 mM Arg * HCl/Sorbitol | −0.14 |
| F14 | 5.79 | 154 | His/120 mM Arg * Glu/Sucrose | −0.18 |
| F15 | 5.2 | 68 | Acetate/Sucrose (Ctrl) | 0.21 |

TABLE B14

Change in Basic Peak Region (% area) for the 5 wk 2-8° C. Samples versus Time-Zero

| Sample | pH | Conc. (mg/mL) | Excipients | Δ % Basic |
|---|---|---|---|---|
| F1 | 5.14 | 151 | Succ/Arg * Glu | 0.31 |
| F2 | 5.29 | 150 | His/75 mM Arg * HCl/Sucrose | 0.40 |
| F3 | 5.22 | 151 | His/75 mM Arg * Glu/Sorbitol | 0.33 |
| F4 | 5.24 | 151 | His/Arg * HCl | 0.27 |
| F5 | 5.18 | 151 | His/Arg * Glu | 0.44 |
| F6 | 5.2 | 152 | His/Arg * Asp | 0.36 |
| F7 | 5.51 | 149 | His/Arg * HCl | 0.44 |
| F8 | 5.46 | 150 | Succ/Arg * HCl | 0.31 |
| F9 | 5.52 | 152 | His/Arg * Glu | 0.16 |
| F10 | 5.53 | 149 | 40 mM His/Arg * Glu | 0.03 |
| F11 | 5.57 | 150 | His/Arg * Asp | −0.06 |
| F12 | 5.77 | 151 | His/Arg * Glu | 0.14 |
| F13 | 5.79 | 152 | His/120 mM Arg * HCl/Sorbitol | 0.14 |
| F14 | 5.79 | 154 | His/120 mM Arg * Glu/Sucrose | 0.21 |
| F15 | 5.2 | 68 | Acetate/Sucrose (Ctrl) | 0.36 |

The majority of changes in main-peak content were insignificant. Most formulations had equivalent chemical stability as the stock solution/drug substance at 2-8° C. (F15).

Overall, Example 4 shows that higher relative pH was most advantageous as regards overall physical and chemical stability. More specifically, pH 5.5-5.8, in particular pH 5.8, is favored.

Physical degradation at 5 and 25° C. was insignificant for all formulations. Chemical degradation at 5 and 25° C. was also generally insignificant, although there could be a slight increase in basic peak content at lower relative pH (pH 5.2).

No obvious advantage to formulating with a sugar or polyol versus the arginine salts alone. Also, succinate buffer provided no improvement in chemical stability versus histidine buffer. Arg/Glu provided slightly better physical stability than the other arginine salts under the stress condition (40° C.). Differences, however, became less prominent at higher relative pH (i.e., pH 5.8).

Viscosity also appeared to decrease slightly at increasing values of pH. Overall, Arg*HCl provided the lowest viscosities.

Example 5. Further Refinement of Formulation Conditions

Based on the results of Examples 3 and 4, this example designed further formulations and tested them in order to arrive at acceptable stable formulations.

The tested samples are shown in Table C1.

TABLE C1

Listing of Tested Formulation Samples (F1-F15)

| Sample | Protein Con (mg/mL) | Buffer | pH | Excipient 1 | Excipient 2 | Polysorbate (PS) | PS (w/v %) |
|---|---|---|---|---|---|---|---|
| F1 | 150 | 20 mM His | 5.5 | 150 mM LysHCl | | PS80 | 0.02 |
| F2 | 150 | 20 mM His | 5.5 | 150 mM L-Arg | LysHCl | PS80 | 0.02 |
| F3 | 150 | 20 mM His | 5.5 | 150 mM L-Arg | L-Glu | PS80 | 0.02 |
| F4 | 150 | 20 mM His | 5.5 | 75 mM ArgHCl | 135 mM Sucrose | PS80 | 0.02 |
| F5 | 150 | 20 mM His | 5.5 | 150 mM ArgHCl | | PS80 | 0.02 |
| F6 | 150 | 20 mM His | 5.5 | 150 mM ArgHCl | | PS80 | 0.03 |
| F7 | 150 | 20 mM His | 5.5 | 150 mM ArgHCl | | PS80 | 0.01 |
| F8 | 150 | 20 mM His | 5.5 | 150 mM ArgHCl | | PS20 | 0.02 |
| F9 | 150 | 20 mM acetate | 4.7 | 150 mM ArgHCl | | PS80 | 0.02 |
| F10 | 150 | 20 mM His | 5.0 | 150 mM ArgHCl | | PS80 | 0.02 |
| F11 | 150 | 20 mM His | 6.0 | 150 mM ArgHCl | | PS80 | 0.02 |
| F12 | 150 | 20 mM His | 6.5 | 150 mM ArgHCl | | PS80 | 0.02 |
| F13 | 70 | 10 mM acetate | 5.2 | | | PS20 | 0.004 |

*F13 is the stock solution

Visual examination of these samples showed that only F9 (pH 4.7) had haze in vials (not associated with increase in turbidity). No relevant change or trend in visible particles at 25° C. after 4 weeks of incubation for all samples. Also, no relevant change or trend was observed in visible particles at 40° C. after 4 weeks, except for F1 and F10.

HIAC measurements of subvisible particles in these samples were conducted after 4 weeks. As shown in Table C2, generally the samples had low subvisible particle counts, and there was no relevant trend in subvisible particles at 5° C. There were higher subvisible particle numbers at 25° C. for F1 (Lys HCl) and F12 (high pH) for 10 μm size. At 40° C., F1 (Lys HCl) and F10-F12 (low and high pH) showed higher subvisible particle numbers.

TABLE C2

Subvisible particles after 4 weeks

| | | Subvisible Particles by HIAC | | | |
|---|---|---|---|---|---|
| Sample | Temp | ≥2 μm | ≥5 μm | ≥10 μm | ≥25 μm |
| F1 | 5° C. | 174 | 22 | 8 | 0 |
| F3 | 5° C. | 65 | 20 | 4 | 0 |
| F4 | 5° C. | 81 | 20 | 4 | 0 |
| F5 | 5° C. | 18 | 5 | 0 | 0 |
| F7 | 5° C. | 17 | 4 | 2 | 0 |
| F8 | 5° C. | 14 | 1 | 0 | 0 |
| F9 | 5° C. | 642 | 112 | 12 | 0 |
| F10 | 5° C. | 25 | 4 | 2 | 1 |
| F11 | 5° C. | 50 | 10 | 2 | 1 |
| F12 | 5° C. | 2205 | 678 | 144 | 0 |
| F13 | 5° C. | 84 | 18 | 1 | 0 |
| F1 | 25° C. | 3770 | 379 | 66 | 5 |
| F3 | 25° C. | 2858 | 67 | 4 | 0 |
| F4 | 25° C. | 288 | 33 | 12 | 0 |
| F5 | 25° C. | 48 | 3 | 1 | 0 |
| F7 | 25° C. | 63 | 10 | 0 | 0 |
| F8 | 25° C. | 43 | 5 | 0 | 0 |
| F9 | 25° C. | 543 | 81 | 18 | 1 |
| F10 | 25° C. | 31 | 1 | 0 | 0 |
| F11 | 25° C. | 91 | 13 | 3 | 1 |
| F12 | 25° C. | 3012 | 625 | 143 | 0 |
| F13 | 25° C. | 52 | 8 | 2 | 0 |
| F1 | 40° C. | 15398 | 893 | 131 | 0 |
| F3 | 40° C. | 3008 | 107 | 3 | 0 |
| F4 | 40° C. | 3031 | 54 | 2 | 1 |
| F5 | 40° C. | 2181 | 83 | 3 | 0 |
| F7 | 40° C. | 3604 | 151 | 4 | 1 |
| F8 | 40° C. | 28 | 3 | 0 | 0 |
| F9 | 40° C. | 316 | 78 | 18 | 0 |
| F10 | 40° C. | 12689 | 836 | 14 | 0 |
| F11 | 40° C. | 12641 | 178 | 5 | 0 |

TABLE C2-continued

Subvisible particles after 4 weeks

| | | Subvisible Particles by HIAC | | | |
|---|---|---|---|---|---|
| Sample | Temp | ≥2 μm | ≥5 μm | ≥10 μm | ≥25 μm |
| F12 | 40° C. | 20960 | 1088 | 15 | 0 |
| F13 | 40° C. | 38 | 8 | 3 | 0 |

SE-HPLC was then used to assess the purity of the samples at time zero and after 4 weeks under different temperature. The results are presented in Table C3.

TABLE C3

SE-HPLC purity measurement

| | | | SE-HPLC | | |
|---|---|---|---|---|---|
| Sample | Timepoint | Temp | Main Peak [% Area] | HMWS [% Area] | LMWS [% Area] |
| F1 | 0 | 25° C. | 98.7 | 1.2 | 0.1 |
| F3 | 0 | 25° C. | 98.7 | 1.2 | 0.1 |
| F4 | 0 | 25° C. | 98.7 | 1.2 | 0.1 |
| F5 | 0 | 25° C. | 98.7 | 1.2 | 0.1 |
| F7 | 0 | 25° C. | 98.7 | 1.2 | 0.1 |
| F8 | 0 | 25° C. | 98.7 | 1.2 | 0.1 |
| F9 | 0 | 25° C. | 98.7 | 1.3 | 0.0 |
| F10 | 0 | 25° C. | 98.5 | 1.2 | 0.3 |
| F11 | 0 | 25° C. | 98.6 | 1.2 | 0.1 |
| F12 | 0 | 25° C. | 97.9 | 2.0 | 0.1 |
| F13 | 0 | 25° C. | 98.9 | 1.1 | 0.0 |
| F1 | 4 wks | 5° C. | 98.7 | 1.2 | 0.1 |
| F3 | 4 wks | 5° C. | 98.7 | 1.2 | 0.1 |
| F4 | 4 wks | 5° C. | 98.7 | 1.2 | 0.1 |
| F5 | 4 wks | 5° C. | 98.7 | 1.2 | 0.1 |
| F7 | 4 wks | 5° C. | 98.7 | 1.2 | 0.1 |
| F8 | 4 wks | 5° C. | 98.7 | 1.2 | 0.1 |
| F9 | 4 wks | 5° C. | 98.7 | 1.3 | 0.0 |
| F10 | 4 wks | 5° C. | 98.5 | 1.2 | 0.3 |
| F11 | 4 wks | 5° C. | 98.5 | 1.3 | 0.1 |
| F12 | 4 wks | 5° C. | 97.9 | 1.9 | 0.2 |
| F13 | 4 wks | 5° C. | 98.9 | 1.1 | 0.0 |
| F1 | 4 wks | 25° C. | 98.5 | 1.4 | 0.1 |
| F3 | 4 wks | 25° C. | 98.5 | 1.4 | 0.1 |
| F4 | 4 wks | 25° C. | 98.5 | 1.4 | 0.1 |
| F5 | 4 wks | 25° C. | 98.5 | 1.4 | 0.1 |
| F7 | 4 wks | 25° C. | 98.5 | 1.4 | 0.1 |
| F8 | 4 wks | 25° C. | 98.5 | 1.4 | 0.1 |
| F9 | 4 wks | 25° C. | 98.4 | 1.6 | 0.0 |
| F10 | 4 wks | 25° C. | 98.3 | 1.4 | 0.3 |
| F11 | 4 wks | 25° C. | 98.5 | 1.4 | 0.2 |
| F12 | 4 wks | 25° C. | 97.6 | 2.1 | 0.3 |
| F13 | 4 wks | 25° C. | 98.6 | 1.3 | 0.0 |
| F1 | 4 wks | 40° C. | 96.2 | 2.7 | 1.1 |
| F3 | 4 wks | 40° C. | 97.5 | 2.4 | 0.2 |
| F4 | 4 wks | 40° C. | 97.1 | 2.3 | 0.7 |
| F5 | 4 wks | 40° C. | 96.7 | 3.1 | 0.1 |
| F7 | 4 wks | 40° C. | 96.8 | 3.1 | 0.1 |
| F8 | 4 wks | 40° C. | 96.8 | 3.1 | 0.1 |
| F9 | 4 wks | 40° C. | 81.0 | 19.0 | 0.1 |
| F10 | 4 wks | 40° C. | 94.8 | 5.0 | 0.3 |
| F11 | 4 wks | 40° C. | 97.3 | 2.4 | 0.3 |
| F12 | 4 wks | 40° C. | 96.9 | 2.8 | 0.4 |
| F13 | 4 wks | 40° C. | 97.8 | 2.1 | 0.1 |

Higher amounts of HMWS were observed for F12 (pH 6.5), with no change with increased stress at 5° C. and 25° C. No relevant changes in HMWS at 5° C. for all formulations. At 40° C., the biggest increases were in HWMS for F9 (acetate, pH 4.7) and then F10 (pH 5).

At 5° C., no relevant changes were observed for fragmentation. At 25° C., there were slightly higher fragmentation for F12 (pH 6.5). At 40° C., F1 (Lys HCl) and F4 (sucrose) showed higher fragmentation. F10 (pH 5) showed generally higher fragmentation than other samples at 5° C. and 25° C.

In summary, this example shows that all tested formulations had low changes of visible particles and subvisible particles. There was no relevant change in color, pH and turbidity. Nevertheless, there was higher turbidity when lysine was added as excipient or at low pH (F9) in acetate buffer after thermal stress.

Higher pH at 6.5 (F12) or added sucrose/Lys-HCl resulted in more fragmentation propensity. Lower pH a 4.7 (F9) led to increases in HMWS and LMWS after thermal stress.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. An aqueous pharmaceutical composition comprising 105 to 250 mg/mL of an antibody,
   a salt of arginine selected from the group consisting of arginine glutamate, arginine aspartate, and arginine HCl,
   histidine, and
   polysorbate (PS) selected from the group consisting of PS 80 and PS 20,
   at a pH of 5.4-5.6,
   wherein the antibody comprises a heavy chain comprising the amino acid sequence of SEQ ID NO:7 and a light chain comprising the amino acid sequence of SEQ ID NO:8.

2. The aqueous pharmaceutical composition of claim 1, which comprises at least 140 mg/mL of the antibody.

3. The aqueous pharmaceutical composition of claim 1, wherein the salt of arginine is arginine HCl.

4. The aqueous pharmaceutical composition of claim 3, wherein the arginine HCl is present at a concentration of 100 mM to 200 mM.

5. The aqueous pharmaceutical composition of claim 3, wherein the histidine is present at a concentration of 10 mM to 50 mM.

6. The aqueous pharmaceutical composition of claim 1, wherein the polysorbate is present at a concentration of 0.01 to 0.04 w/v %.

7. The aqueous pharmaceutical composition of claim 3, which does not include lysine.

8. The aqueous pharmaceutical composition of claim 7, which does not include any of sucrose, acetate, NaCl, citrate, sugar, polyol, succinate, proline, or sorbitol.

9. A solid composition that is lyophilized from the aqueous pharmaceutical composition of claim 1, or that forms the aqueous pharmaceutical composition of claim 1 when admixed with water.

10. An aqueous pharmaceutical composition, consisting essentially of 105 to 250 mg/mL of an antibody, 100 mM to 200 mM of arginine glutamate, arginine aspartate, or arginine HCl, 10 mM to 50 mM histidine, and 0.015 to 0.035 w/v % of polysorbate, at a pH of 5.4 to 5.6, wherein the antibody comprises a heavy chain comprising the amino acid sequence of SEQ ID NO:7 and a light chain comprising the amino acid sequence of SEQ ID NO:8.

11. The aqueous pharmaceutical composition of claim 10, which does not include any of acetate, succinate, citrate, NaCl, sorbitol, lysine, proline, sugar, or polyol.

12. An aqueous pharmaceutical composition, consisting of 105 to 250 mg/mL of an antibody, 100 mM to 200 mM of arginine glutamate, arginine aspartate, or arginine HCl, 10 mM to 50 mM histidine, and 0.015 to 0.035 w/v % of polysorbate, at a pH of 5.4 to 5.6, wherein the antibody comprises a heavy chain comprising the amino acid sequence of SEQ ID NO:7 and a light chain comprising the amino acid sequence of SEQ ID NO:8.

13. The aqueous pharmaceutical composition of claim 12, which consists of 140 to 250 mg/mL of the antibody, 120 mM to 180 mM of arginine HCl, 15 mM to 25 mM histidine, and 0.02 to 0.03 w/v % of polysorbate 80, at a pH of 5.45 to 5.55.

\* \* \* \* \*